(12) United States Patent
Anderson et al.

(10) Patent No.: US 12,376,963 B1
(45) Date of Patent: Aug. 5, 2025

(54) PROSTHETIC HEART VALVES

(71) Applicant: Laplace Interventional Inc., Plymouth, MN (US)

(72) Inventors: Rachel Jean Anderson, St. Louis Park, MN (US); Lucas Tradd Schneider, Champlin, MN (US); Gunnar Paul Askegaard, Maple Grove, MN (US); Daniel Oliver, Portland, OR (US); Ramji Iyer, Plymouth, MN (US)

(73) Assignee: Laplace Interventional Inc., Plymouth, MN (US)

( * ) Notice: Subject to any disclaimer, the term of this patent is extended or adjusted under 35 U.S.C. 154(b) by 0 days.

(21) Appl. No.: 19/203,515

(22) Filed: May 9, 2025

Related U.S. Application Data

(62) Division of application No. 19/085,135, filed on Mar. 20, 2025.

(60) Provisional application No. 63/757,042, filed on Feb. 11, 2025.

(51) Int. Cl.
*A61F 2/24* (2006.01)

(52) U.S. Cl.
CPC .......... *A61F 2/2439* (2013.01); *A61F 2/2418* (2013.01); *A61F 2230/0043* (2013.01)

(58) Field of Classification Search
CPC .............................. A61F 2/2439; A61F 2/2418
See application file for complete search history.

(56) References Cited

U.S. PATENT DOCUMENTS

| | | | |
|---|---|---|---|
| 5,824,069 A | 10/1998 | Lemole | |
| 6,312,464 B1 | 11/2001 | Navia | |
| 6,458,153 B1 | 10/2002 | Bailey et al. | |
| 8,728,155 B2 | 5/2014 | Montorfano et al. | |
| 9,393,110 B2 | 7/2016 | Levi et al. | |
| 9,579,196 B2 | 2/2017 | Morriss | |
| 9,681,951 B2 | 6/2017 | Ratz et al. | |
| 10,213,307 B2 | 2/2019 | Dwork | |
| 10,321,995 B1 | 6/2019 | Christianson | |
| 10,583,000 B2 | 3/2020 | Ratz | |

(Continued)

FOREIGN PATENT DOCUMENTS

| EP | 3520736 A1 | 8/2019 |
|---|---|---|
| WO | WO 2009/094500 A1 | 7/2009 |
| WO | WO 2015/052570 A1 | 4/2015 |

OTHER PUBLICATIONS

U.S. Appl. No. 17/747,507, filed May 18, 2022, Iyer et al.

*Primary Examiner* — Suba Ganesan

(74) *Attorney, Agent, or Firm* — Fish & Richardson P.C.

(57) ABSTRACT

Prosthetic heart valves may be delivered to a targeted native heart valve site via one or more delivery catheters. In some embodiments, the prosthetic heart valves are implanted using catheter-based deployment systems that include multiple control wires. In particular implementations, the deployment systems can include a retrieval catheter that can be used to recapture the prosthetic heart valve back into a delivery sheath after being expressed from the delivery sheath. The prosthetic heart valves can include a plurality of optional suture knots to enhance migration resistance. Some delivery catheter systems can include a controllably bendable control catheter and/or a deflectable catheter to facilitate deployment of the prosthetic heart valve to a native tricuspid valve site via a superior vena cava or inferior vena cava.

14 Claims, 21 Drawing Sheets

(56) References Cited

U.S. PATENT DOCUMENTS

| | | |
|---|---|---|
| 10,595,994 B1 | 3/2020 | Christianson |
| 10,653,522 B1 | 5/2020 | Vidlund et al. |
| 10,779,935 B2 | 9/2020 | Scorsin et al. |
| 10,779,936 B2 | 9/2020 | Pollak |
| 10,813,779 B2 | 10/2020 | Fleming, III et al. |
| 10,898,328 B2 | 1/2021 | Starksen et al. |
| 11,109,965 B2 | 9/2021 | Iyer et al. |
| 11,185,409 B2 | 11/2021 | Christianson et al. |
| 11,234,813 B2 | 2/2022 | Perrin |
| 11,253,359 B2 | 2/2022 | Vidlund et al. |
| 11,337,800 B2 | 5/2022 | Schreck et al. |
| 11,337,801 B2 | 5/2022 | Iyer et al. |
| 11,344,413 B2 | 5/2022 | Christianson et al. |
| 11,504,231 B2 | 11/2022 | Carlino et al. |
| 11,510,777 B1 | 11/2022 | Iyer et al. |
| 11,564,794 B2 | 1/2023 | Straubinger et al. |
| 11,602,433 B2 | 3/2023 | Ratz et al. |
| 11,638,643 B1 | 5/2023 | Askegaard et al. |
| 11,672,655 B1 | 6/2023 | Iyer et al. |
| 11,701,223 B2 | 7/2023 | Iyer et al. |
| 11,712,336 B1 | 8/2023 | Schneider et al. |
| 11,759,316 B1 | 9/2023 | Askegaard et al. |
| 11,806,235 B1 | 11/2023 | Schneider et al. |
| 11,918,460 B2 | 3/2024 | Askegaard et al. |
| 11,918,463 B2 | 3/2024 | Iyer et al. |
| 12,059,346 B2 | 8/2024 | Iyer et al. |
| 2004/0092962 A1 | 5/2004 | Thornton et al. |
| 2005/0149181 A1 | 7/2005 | Eberhardt |
| 2007/0043435 A1 | 2/2007 | Seguin et al. |
| 2007/0055356 A1 | 3/2007 | Eidenschink |
| 2008/0065204 A1 | 3/2008 | Macoviak et al. |
| 2009/0281618 A1 | 11/2009 | Hill |
| 2010/0023046 A1 | 1/2010 | Heidner et al. |
| 2010/0036479 A1 | 2/2010 | Hill |
| 2010/0161045 A1 | 6/2010 | Righini |
| 2010/0217382 A1 | 8/2010 | Chau et al. |
| 2010/0316830 A1 | 12/2010 | Hartley et al. |
| 2011/0137397 A1 | 6/2011 | Chau et al. |
| 2011/0319989 A1 | 12/2011 | Lane et al. |
| 2012/0083832 A1 | 4/2012 | Delaloye et al. |
| 2013/0190861 A1 | 7/2013 | Chau et al. |
| 2013/0211508 A1 | 8/2013 | Lane et al. |
| 2013/0325110 A1 | 12/2013 | Khalil et al. |
| 2013/0325114 A1 | 12/2013 | McLean et al. |
| 2014/0135910 A1 | 5/2014 | Hauser |
| 2014/0207231 A1 | 7/2014 | Hacohen et al. |
| 2014/0222142 A1 | 8/2014 | Kovalsky et al. |
| 2014/0257467 A1 | 9/2014 | Lane et al. |
| 2014/0277390 A1 | 9/2014 | Ratz |
| 2014/0296969 A1 | 10/2014 | Tegels et al. |
| 2014/0296975 A1 | 10/2014 | Tegels et al. |
| 2014/0324164 A1 | 10/2014 | Gross et al. |
| 2014/0350669 A1 | 11/2014 | Gillespie et al. |
| 2015/0073544 A1 | 3/2015 | Gorman, III |
| 2015/0119981 A1 | 4/2015 | Khairkhahan et al. |
| 2015/0196390 A1 | 7/2015 | Ma et al. |
| 2015/0216653 A1 | 8/2015 | Freudenthal |
| 2015/0327994 A1 | 11/2015 | Morriss et al. |
| 2016/0158003 A1 | 6/2016 | Wallace et al. |
| 2016/0262887 A1 | 9/2016 | Chang et al. |
| 2016/0278922 A1 | 9/2016 | Braido et al. |
| 2017/0056166 A1 | 3/2017 | Ratz et al. |
| 2017/0065409 A1 | 3/2017 | Scorsin et al. |
| 2017/0071733 A1 | 3/2017 | Ghione et al. |
| 2017/0128199 A1 | 5/2017 | Gurovich et al. |
| 2017/0128208 A1 | 5/2017 | Christianson et al. |
| 2017/0128209 A1 | 5/2017 | Morriss et al. |
| 2017/0216023 A1 | 8/2017 | Lane et al. |
| 2017/0216026 A1 | 8/2017 | Quill et al. |
| 2017/0325945 A1 | 11/2017 | Dale et al. |
| 2018/0000586 A1 | 1/2018 | Ganesan |
| 2018/0116798 A1 | 5/2018 | Perszyk |
| 2018/0303612 A1 | 10/2018 | Pasquino et al. |
| 2018/0318071 A1 | 11/2018 | Lozonschi |
| 2018/0368977 A1 | 12/2018 | Gorman et al. |
| 2019/0008635 A1 | 1/2019 | Francis et al. |
| 2019/0008636 A1 | 1/2019 | Francis et al. |
| 2019/0029811 A1 | 1/2019 | Bishop et al. |
| 2019/0183639 A1 | 6/2019 | Moore |
| 2020/0121452 A1 | 4/2020 | Saikrishnan et al. |
| 2020/0179109 A1 | 6/2020 | Reimer |
| 2020/0188097 A1 | 6/2020 | Perrin et al. |
| 2020/0237506 A1 | 7/2020 | Christianson et al. |
| 2020/0268512 A1 | 8/2020 | Mohl |
| 2021/0154011 A1 | 5/2021 | Christianson et al. |
| 2021/0186693 A1* | 6/2021 | Vidlund, I ............... A61F 2/243 |
| 2021/0220126 A1 | 7/2021 | Perrin |
| 2021/0220127 A1 | 7/2021 | Vidlund et al. |
| 2021/0236257 A1 | 8/2021 | Walzman |
| 2021/0236280 A1 | 8/2021 | Christianson et al. |
| 2021/0259830 A1 | 8/2021 | Enriquez-Sarano |
| 2021/0290385 A1 | 9/2021 | Christianson et al. |
| 2021/0346153 A1 | 9/2021 | Vietmeier et al. |
| 2021/0315694 A1 | 10/2021 | Vidlund et al. |
| 2021/0330459 A1 | 10/2021 | Christianson |
| 2021/0369454 A1 | 12/2021 | Stack et al. |
| 2021/0401572 A1 | 12/2021 | Nasr et al. |
| 2022/0096226 A1 | 3/2022 | Christianson et al. |
| 2022/0160499 A1 | 5/2022 | Miyashiro et al. |
| 2022/0192824 A1 | 6/2022 | Vidlund et al. |
| 2022/0257397 A1 | 8/2022 | Qi |
| 2022/0313428 A1 | 10/2022 | Bergin |
| 2022/0409369 A1 | 12/2022 | Christianson et al. |
| 2023/0130224 A1 | 4/2023 | Rajagopal |
| 2023/0131595 A1 | 4/2023 | Van Hoven et al. |
| 2023/0218390 A1 | 7/2023 | Pisani |
| 2023/0293297 A1 | 9/2023 | Alon et al. |
| 2023/0320846 A1 | 11/2023 | Iyer et al. |
| 2023/0363914 A1 | 11/2023 | Alavi |
| 2023/0390052 A1 | 12/2023 | Okafor |
| 2024/0173120 A1 | 5/2024 | Askegaard et al. |
| 2024/0358504 A1 | 10/2024 | Iyer et al. |
| 2025/0073021 A1 | 3/2025 | Askegaard et al. |

\* cited by examiner

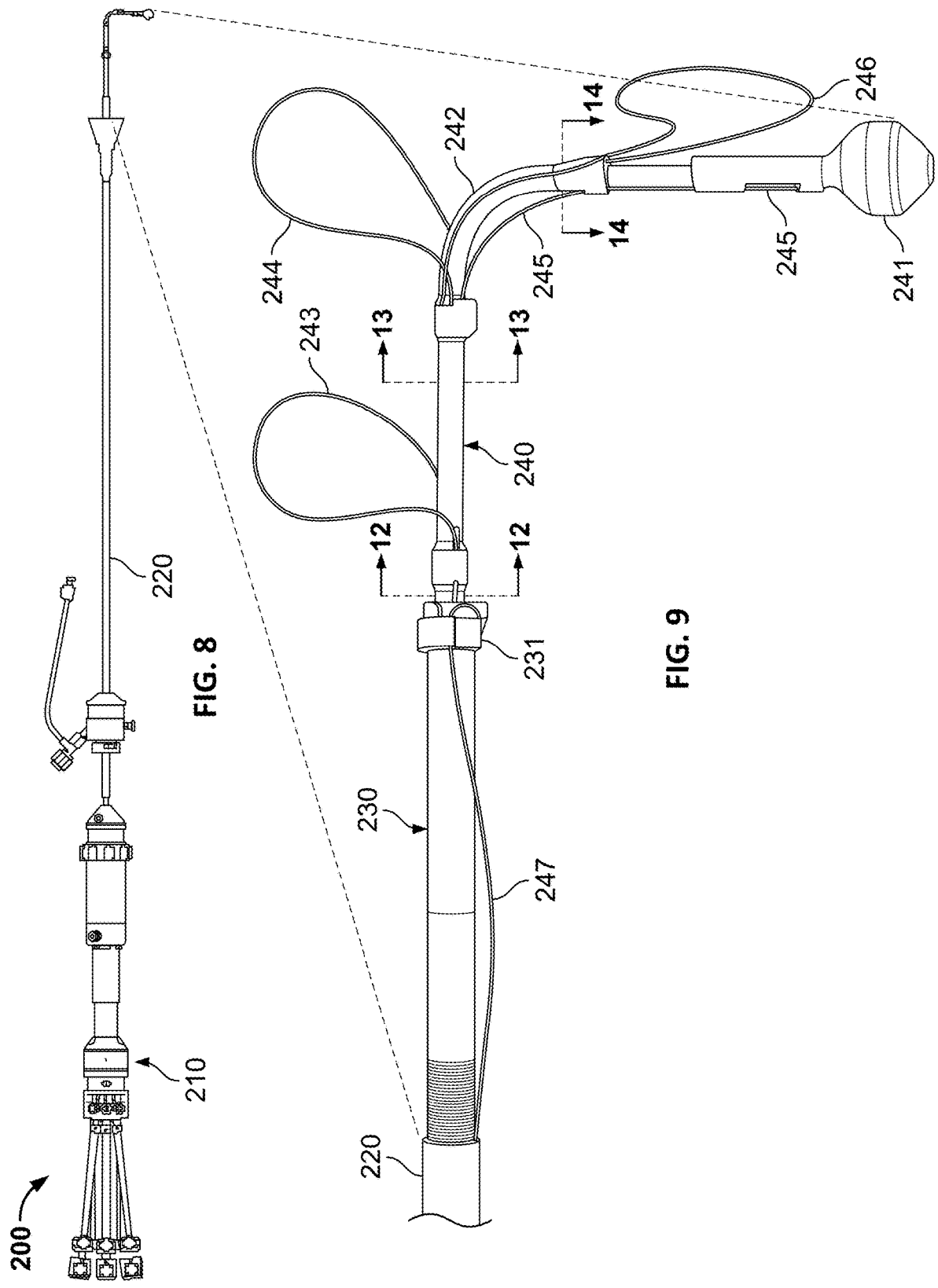

PROSTHETIC HEART VALVES

CROSS-REFERENCE TO RELATED APPLICATIONS

This application is a divisional application of U.S. application Ser. No. 19/085,135 filed on Mar. 20, 2025, which claims the benefit of U.S. Provisional Application Ser. No. 63/757,042 filed on Feb. 11, 2025. The disclosure of the prior applications are considered part of (and are incorporated by reference in) the disclosure of this application.

FIELD OF INVENTION

This disclosure generally relates to prosthetic heart valve systems. For example, this disclosure relates to prosthetic heart valves and catheter-based deployment systems that are used to replace a sub-optimally functioning native heart valve, including but not limited to a tricuspid valve.

BACKGROUND

A human heart includes four types of heart valves that are arranged to ensure blood flow in specific directions: mitral, tricuspid, aortic and pulmonary valves. The aortic and pulmonary valves are semilunar valves, which are in the arteries leaving the heart, and prevent blood from flowing back into left ventricle and right ventricle respectively when closed. The mitral and tricuspid valves are atrio-ventricular valves, which are between the atria and the ventricles, and prevent blood from flowing back into left atrium and right atrium respectively when closed. Conditions of stenosis (when valve does not open fully) as well as regurgitation/insufficiency (when valve does not close properly resulting in leaks) are recognized as significant contributors to mortality and morbidity.

Some valve replacement systems include a valve prosthesis that is compressed into a delivery catheter, also referred to as transcatheter valves, so as to avoid open-heart surgery. Many transcatheter valve prostheses have a tubular frame that may or may not be axisymmetric, and include an occluder that has two or more leaflets. While these transcatheter valve prostheses can be compressed into a catheter, they may still require a relatively large delivery system (for example, a required catheter size of up to 45 French). This is especially true in case of mitral valve replacement systems and tricuspid valve replacement systems, which often require valve prostheses with a larger delivery profile.

SUMMARY

Some embodiments described herein include a prosthetic valve system that includes a prosthetic valve system and a valve deployment system. The prosthetic heart valve includes a main body including an inflow end portion and an outflow end portion and one or more anterior flaps extending from the outflow end portion. The main body defines a central axis extending between the inflow and outflow end portions. The one or more anterior flaps extend in a first direction that is transverse to the central axis. The valve deployment system includes: an elongate control catheter defining one or more lumens and comprising a naturally curved end portion; a third control wire slidably disposed in the one or more lumens and releasably coupled to the one or more anterior flaps; and a suture or wire member releasably coupled to the third control wire. The valve deployment system is configured so that adding tension to the suture or wire member adjusts a curvature of the elongate control catheter in a direction of the one or more anterior flaps.

Such a prosthetic valve system may optionally include one or more of the following features. The system may include a retrieval catheter with an expandable conical end portion. The suture or wire member may be attached to the retrieval catheter. The inflow end portion of the main body may have a smaller outer size than an outer size of the outflow end portion of the main body. The valve deployment system may also include a first control wire comprising a first wire loop that extends out of the one or more lumens and that is releasably coupled to the inflow end portion of the main body. The valve deployment system may also include a second control wire comprising a second wire loop that extends out of the one or more lumens and that is releasably coupled to the outflow end portion. The third control wire may include a single wire segment that extends out of the one or more lumens, releasably couples with the one or more anterior flaps and the suture or wire member and terminates in releasable engagement with a distal tip portion of the control catheter. The valve deployment system may also include a deflectable catheter defining a lumen. A portion of the control catheter may be slidably disposable within the lumen of the deflectable catheter. The valve deployment system may also include a fifth control wire slidably coupled with the deflectable catheter. The prosthetic heart valve may also include a posterior arm extending from the inflow end portion of the main body. In some embodiments, the fifth control wire comprises a single wire segment that releasably couples with the posterior arm and terminates in releasable engagement with a distal tip portion of the deflectable catheter. A distal end portion of the deflectable catheter may be selectively deflectable by manipulating a user control mechanism coupled to a proximal end of the valve deployment system. The one or more anterior flaps may include a septal anterior flap and a lateral anterior flap. An edge portion of the septal anterior flap may include a septal anterior strut framework, and an edge portion of the lateral anterior flap may include a lateral anterior strut framework. The septal anterior strut framework may include S-shaped struts. The lateral anterior strut framework may include L-shaped struts. The outflow end portion of the main body may extend to a farthest end of the prosthetic heart valve.

In another aspect, this disclosure is directed to a prosthetic heart valve that includes a main body including an inflow end portion and an outflow end portion, the main body defining a central axis extending between the inflow and outflow end portions; a plurality of suture knots protruding from an external surface of the main body; and one or more anterior flaps extending from the outflow end portion in a first direction that is transverse to the central axis.

Such a prosthetic heart valve may optionally include one or more of the following features. In some embodiments, the plurality of suture knots are only attached to the external surface of the outflow end portion of the main body. In some embodiments, the plurality of suture knots are only attached to lateral and septal external surfaces of the outflow end portion. The one or more anterior flaps may include a septal anterior flap and a lateral anterior flap. An edge portion of the septal anterior flap may include a septal anterior strut framework, and an edge portion of the lateral anterior flap may include a lateral anterior strut framework. The septal anterior strut framework may include S-shaped struts. The lateral anterior strut framework may include L-shaped struts.

Any of the prosthetic heart valves described herein may optionally include one or more of the following additional features. In some embodiments, portions of the first anterior flap and the second anterior flap overlap each other. The prosthetic tricuspid valve may also include a posterior flap extending laterally from the end of the main body in an opposite direction as the first and second anterior flaps. In some embodiments, the first and second anterior flaps extend farther laterally than the posterior flap. In particular embodiments, the first and second anterior flaps in combination are wider (in the septal to lateral direction) than the posterior flap. A framework of the prosthetic tricuspid valve (that comprises the main body, the first and second anterior flaps, and the posterior flap) may be made of a single, unitary material that was cut and expanded. In some embodiments, a distal tip portion of the posterior flap extends along an axis that is at a non-zero angle relative to a portion of the posterior flap that extends directly from the main body. In some examples, having the portions of the first anterior flap and the second anterior flap that overlap each other increases a bending resistance of the first anterior flap and the second anterior flap in combination as compared to the first anterior flap and the second anterior flap individually. Having the portions of the first anterior flap and the second anterior flap as separate members or regions can configure the prosthetic tricuspid valve to have a pacemaker lead pass through the prosthetic tricuspid valve between the first and second anterior flaps. The prosthetic tricuspid valve may also include one or more additional anterior flaps extending laterally from the end of the main body in the same direction as the first and second anterior flaps. The prosthetic tricuspid valve may also include two or more posterior flaps extending laterally from the end of the main body in an opposite direction as the first and second anterior flaps. Having the portions of the first posterior flap and the second posterior flap as separate members or regions can configure the prosthetic tricuspid valve to have a pacemaker lead pass through the prosthetic tricuspid valve between the first and second posterior flaps. In some embodiments, a transverse cross-section of the main body has an oval shaped outer profile that defines a major diameter and a minor diameter. The minor diameter is shorter than the major diameter. The occluder may have a circular cross-sectional shape, and the anterior and posterior flaps may extend transversely to the major diameter. The prosthetic heart valve may also include a leaflet engagement member extending from the main body, a portion of the leaflet engagement member extending toward the inflow end portion and terminating at a free end. The leaflet engagement member may extend in the second direction. The posterior flap may extend farther away from the main body than the leaflet engagement member.

BRIEF DESCRIPTION OF FIGURES

FIG. 8 illustrates an example transcatheter prosthetic heart valve deployment system in accordance with some embodiments.

FIG. 9 is an enlarged view of the distal end portion of the transcatheter prosthetic heart valve deployment system of FIG. 8.

DETAILED DESCRIPTION

Some embodiments described herein include a prosthetic heart valve that may be delivered to a targeted native heart valve site via a deployment system that includes one or more delivery catheters. In some embodiments, the prosthetic heart valve may be releasably coupled to the one or more delivery catheters using one or more control wires. The control wires can be individually manipulated by a clinician-user at a handle of the deployment system to expand and/or deploy particular portions of the prosthetic heart valve in a controlled manner.

In particular implementations, the deployment systems described herein can include a retrieval catheter that can be used to recapture the prosthetic heart valve back into a delivery sheath after being expressed from the delivery sheath.

Some delivery catheter systems described herein can include a curved control catheter and/or a selectively deflectable/steerable catheter to facilitate deployment of the prosthetic heart valve to a native tricuspid valve site via a superior vena cava or inferior vena cava.

In some embodiments, the prosthetic heart valves described herein include one or more structural features that securely anchor the prosthetic heart valve to the anatomy at the site of the native heart valve. Such structural features can provide robust migration resistance during diastole and systole. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart.

Figure 1:
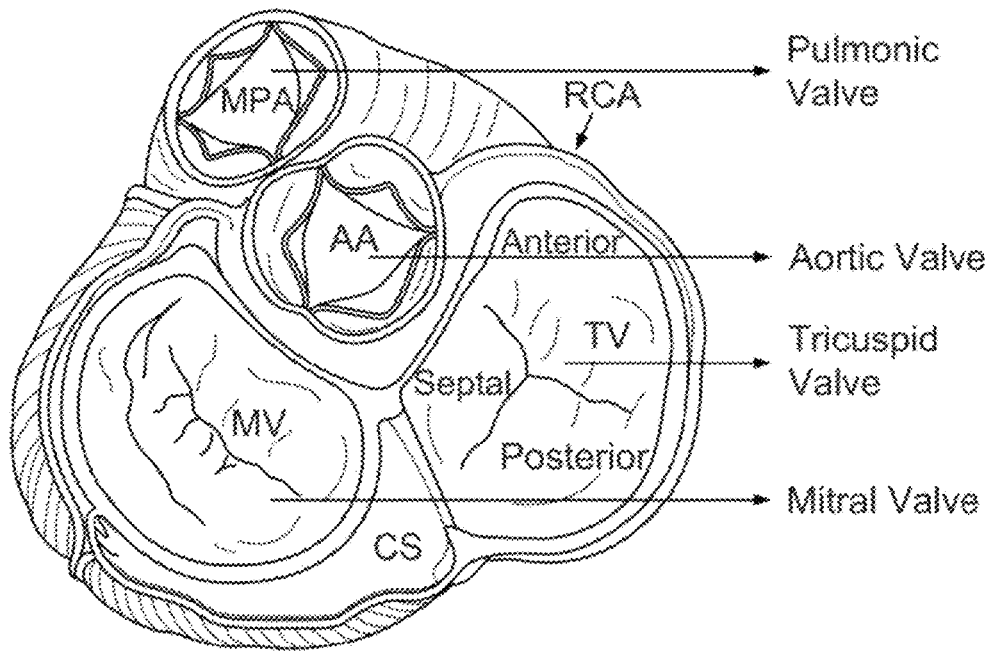
FIG. 1 shows a sectional view of a human heart including four heart valves (mitral valve, tricuspid valve, aortic valve, and pulmonary valve) that allow blood flow through specific pathways. The mitral and tricuspid valve are arranged to normally prevent backflow of blood into left atrium and right atrium respectively when the left and right ventricle contract respectively.
Figure 2:
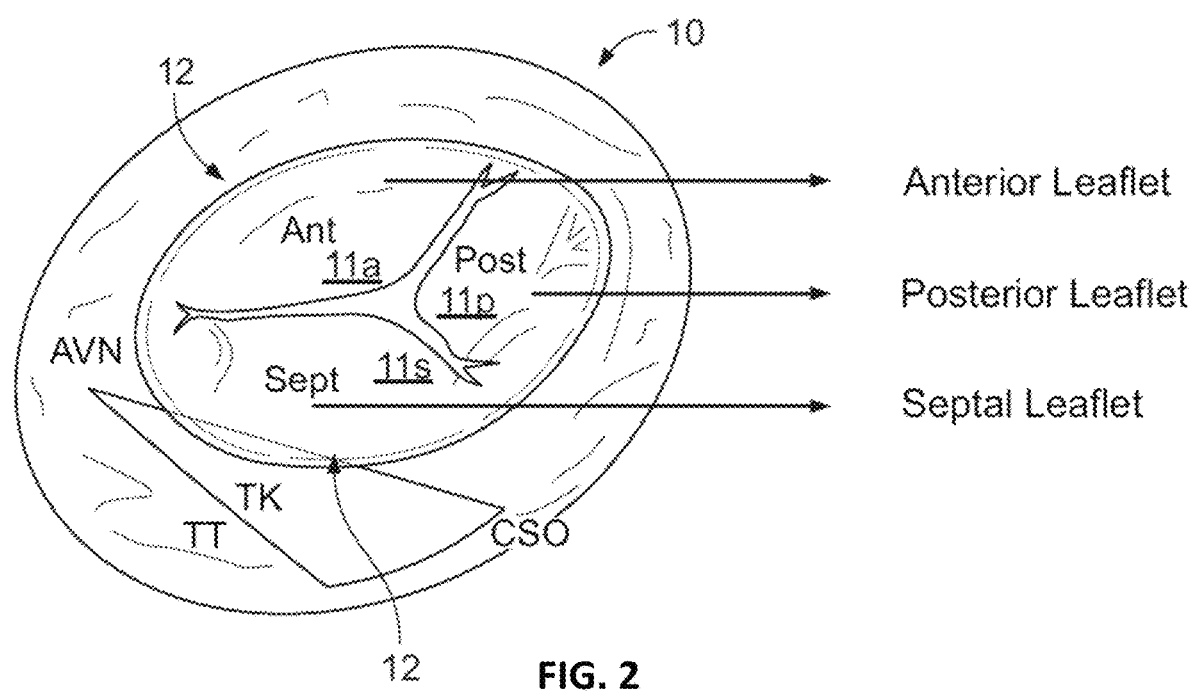
FIG. 2 shows a top view of the tricuspid valve of FIG. 1 and including three native leaflets: anterior, posterior and septal.

Referring to FIG. 1, certain aspects of the concepts described herein regarding the heart valve replacement systems can be implemented in prosthetic valve designs that are intended for use at any of the four heart valves that allow blood flow through a specific pathway: mitral valve, tricuspid valve, aortic valve and the pulmonary valve. FIG. 2 depicts, for example, a targeted site at a tricuspid valve 10 of the heart. The tricuspid valve 10 includes an anterior leaflet 11a, a posterior leaflet 11p, and a septal leaflet 11s, and an annulus 12. In some circumstances, the tricuspid valve 10 may undergo stenosis or anatomical changes that cause tricuspid regurgitation, such as instances in which the distance between the anterio-septal commissure and the anterio-posterior commissure of the native tricuspid valve increases with the progression of a diseased state due to dilation of the annulus 12 of the tricuspid valve 10.

Figure 3:
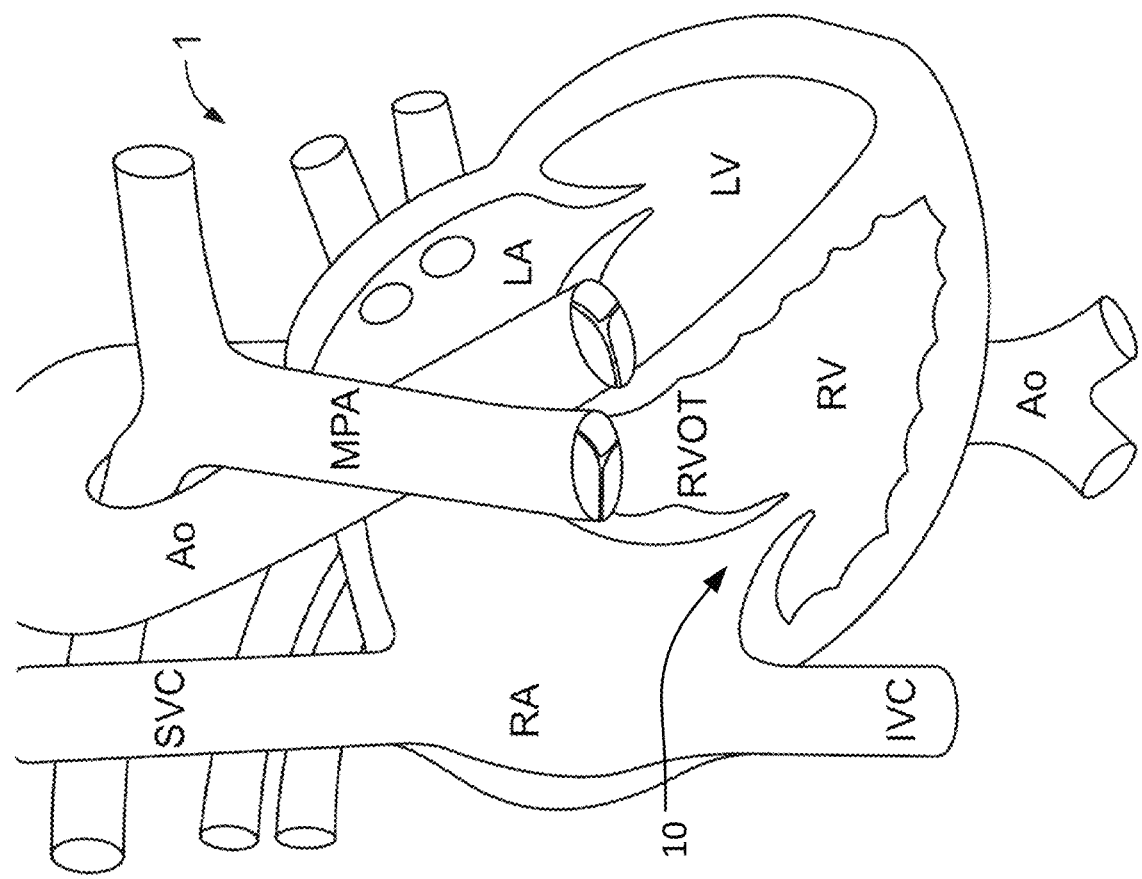
FIG. 3 shows another sectional view of a human heart including the four chambers (right atrium, right ventricle, left atrium, and left ventricle) and major conduits that deliver blood to the heart and transport blood away from the heart.

FIG. 3 illustrates a longitudinal sectional view of a human heart 1 that shows the four chambers (right atrium, right ventricle, left atrium, and left ventricle) and the major conduits that deliver blood to the heart 1 and transport blood away from the heart 1. The tricuspid valve 10 is located between the right atrium and the right ventricle. Blood enters the right atrium from the superior vena cava and the inferior vena cava. Blood flows from the right atrium to the right ventricle through the tricuspid valve 10. The blood exits the right ventricle and enters the main pulmonary artery ("MPA") via the RVOT that is adjacent to the tricuspid valve 10.

Figure 4:
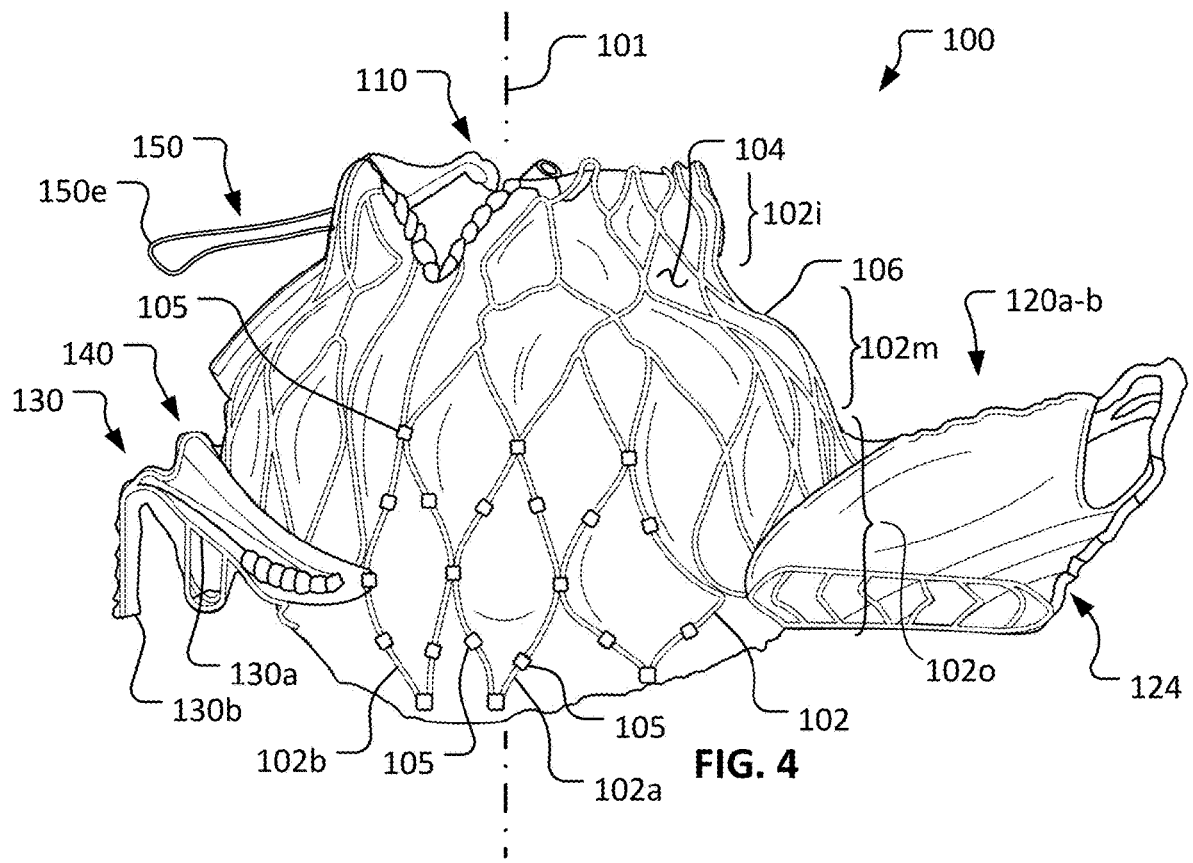
FIG. 4 shows a side view of an example prosthetic heart valve in accordance with some embodiments described herein.
Figure 5:
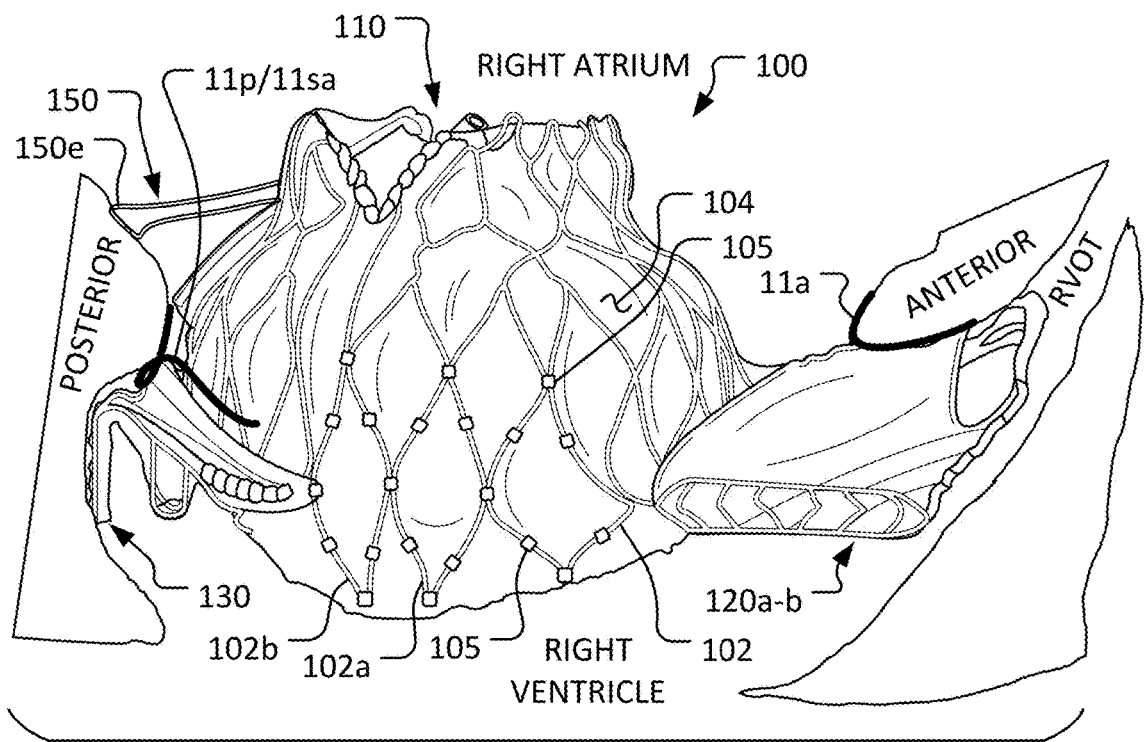
FIG. 5 shows a side view of the prosthetic heart valve of FIG. 4 engaged within a native tricuspid valve.
Figure 6:
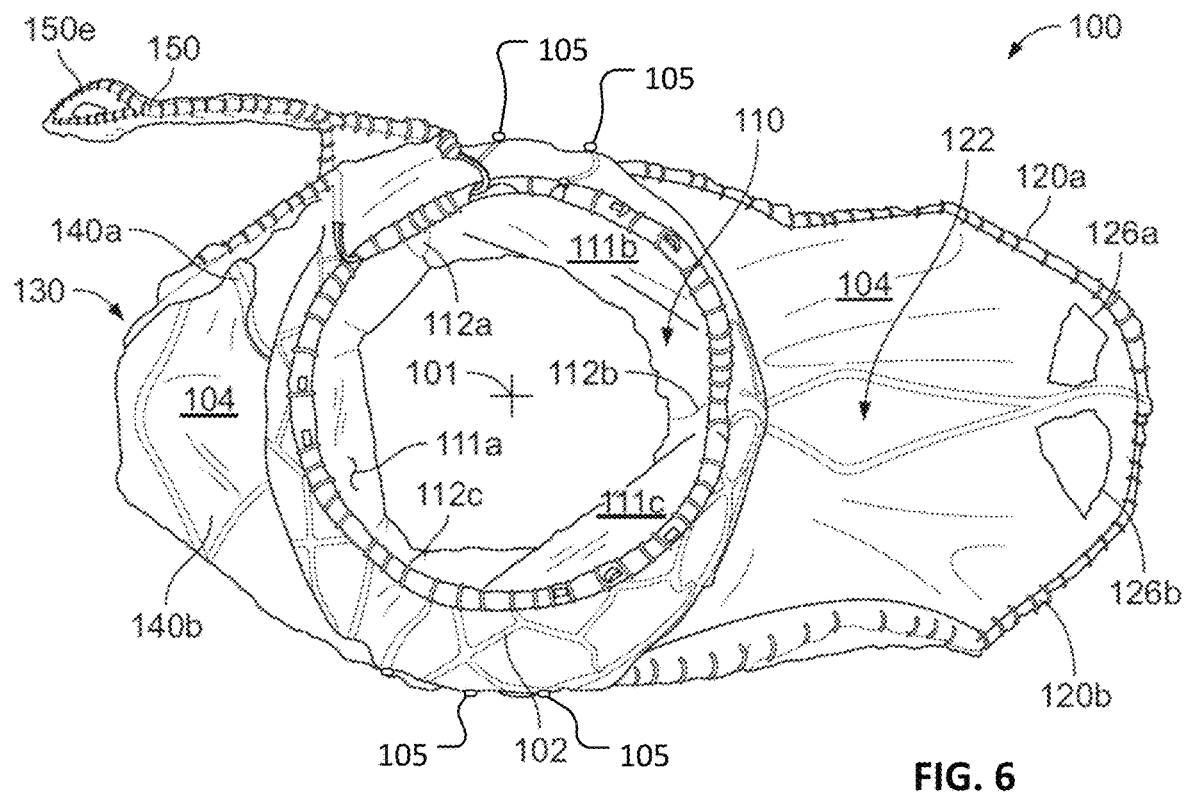
FIG. 6 shows a top view of the prosthetic heart valve of FIG. 4.
Figure 7:
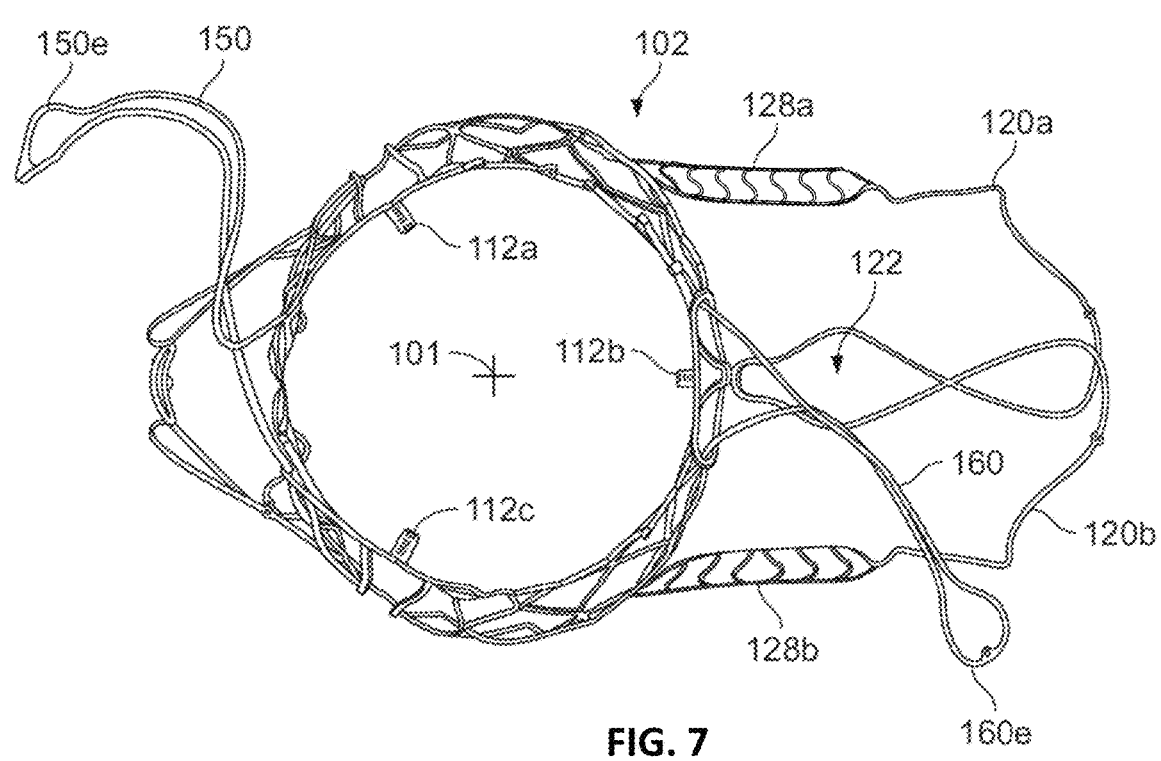
FIG. 7 shows a top view of a frame of another example prosthetic heart valve in accordance with some embodiments described herein.

FIGS. 4-6 illustrate an example prosthetic tricuspid valve 100 (or simply "valve 100") in accordance with some example embodiments of this disclosure. The valve 100 includes a frame 102 and a covering 104 attached to the frame 102. FIG. 7 shows the valve 100 engaged with a native tricuspid valve 10 between the right atrium and the right ventricle.

The frame 102 comprises a cellular structure that provides mechanical support for the shape and structures of the valve 100. In some embodiments, the frame 102 is made from nitinol (NiTi), stainless steel, cobalt chromium, MP35N, titanium, polymeric materials, other biocompatible materials, or any combination thereof. Some or all parts of the frame 102 may be covered by the covering 104. The frame 102 can be made of a laser cut, expanded, and shape-set material in some embodiments. The frame 102 is self-expanding in some embodiments. In some embodiments, the precursor material is tubular NiTi, a NiTi sheet, or other suitable types of precursor materials.

The covering 104 may made of a biocompatible polymer material (e.g., expanded polytetrafluoroethylene (ePTFE), UHMWPE (ultra-high molecular weight polyethylene), nylon, polyester (e.g., DACRON), or another synthetic material), natural tissues (e.g., bovine, porcine, ovine, or equine pericardium), or any combination thereof. The covering 104 can be attached to the frame 102 by suturing, using clips, adhesives, and/or any other suitable attachment process.

The valve 100 includes a main body 106. The main body 106 includes an occluder 110 (e.g., a one-way valve) that defines a central axis 101. The occluder 110 has flexible leaflets 111a, 111b, and 111c (collectively 111a-c) that cause the occluder 110 to function as a one-way valve (in a manner like a native tricuspid valve). The occluder 110 defines a circular inlet where the edges of leaflets 111a-c are attached to the frame 102. Other side edges of the leaflets 111a-c are attached to posts 112a, 112b, and 112c of the frame 102. The leaflets 111a-c also have distal free edges that are coaptable with each other to facilitate the opening and sealing of the occluder 110.

The main body 106 of the valve 100 includes an inflow end portion 102i, a mid-body portion 102m, and an outflow end portion 102o. The inflow end portion 102i includes a series of arch shapes in the frame 102, circumscribing the axis 101 of the occluder 110. The occluder leaflets 111a-c allow blood to directionally flow through the occluder 110 from the inflow end portion 102i to the outflow end portion 102o. The leaflets 111a-c of the occluder 110 close against each other (e.g., coapt) to prevent blood flow in the other direction (to prevent blood flow from the outflow end portion 102o to the inflow end portion 102i).

The embodiments of the valve 100 depicted in this disclosure employ three occluder leaflets 111a-c, which is referred to as tri-leaflet occluder. The occluder 110 of the valve 100 can optionally employ configurations other than a tri-leaflet occluder. For example, bi-leaflet, quad-leaflet, or mechanical valve constructs can be used in some embodiments. In particular implementations described herein, the flexible leaflets 111a-c are made of natural tissues such as porcine or bovine or equine or ovine pericardium. In such embodiments, the tissues are chemically cross-linked using glutaraldehyde or formaldehyde, or other aldehydes commonly used as crosslinking agents. In other embodiments, the flexible leaflets 111a-c are made of polymers such as polyurethane, polyester (DACRON) or expanded polytetrafluoroethylene (ePTFE). In some embodiments, the flexible leaflets 111a-c are attached to structural frame 102 using sutures that could be made of materials including but not limited to UHMWPE, nylon, or polyester (e.g., DACRON).

The valve 100 also includes a first anterior flap 120a (or septal anterior flap 120a), a second anterior flap 120b (or lateral anterior flap 120b), and at least one posterior flap 130. The frame 102 and the covering 104 combine to form the anterior flaps 120a-b and the posterior flap 130. The frame 102 provides the structure of the anterior flaps 120a-b and the posterior flap 130, and the covering 104 provides occlusion. While the depicted embodiment includes two anterior flaps 120a-b, in some embodiments one, three, four, or more than four anterior flaps can be included. While the depicted embodiment includes a single posterior flap 130, in some embodiments two, three, four, or more than four posterior flaps can be included.

The anterior flaps 120a-b and the posterior flap 130 extend away from the outflow end portion 1020 of the main body 106 in opposite directions away from the axis 101. That is, the posterior flap 130 extends directionally opposite from the extension direction of the first and second anterior flaps 120a-b. In some embodiments, the posterior flap 130 extends 180° opposite from the extension direction of the first and second anterior flaps 120a-b. In particular embodiments, the anterior flaps 120a-b and the posterior flap 130 extend away from the outflow end portion 1020 of the main body 106 transverse to the axis 101 of the occluder 110.

In the depicted embodiment, the first anterior flap 120a and the second anterior flap 120b each include a mid-body portion 124 (FIG. 6) that is bent at an angle so as to direct terminal end portions of the anterior flaps 120a-b toward the inlet end of the main body 106. In some embodiments, the anterior flaps 120a-b initially extend away from the main body 106 substantially perpendicularly (e.g., within about 80° to) 100° to the central axis 101. Then, at the mid-body portion 124, the anterior flaps 120a-b have a bend that defines an angle θ in a range of between 20° to 60°, or 30° to 60°, or 30° to 70°, or 40° to 60°, or 40° to 70°, or 40° to 50°, without limitation.

The bends in the mid-body 106 of the anterior flaps 120a-b can allow the anterior flaps 120a-b to conform to the contours of the wall that defines the RVOT (as shown in FIG. 5). Accordingly, the bent anterior flaps 120a-b can reduce the potential of the anterior flaps 120a-b to restrict blood flow through the RVOT in some cases.

In some patients, the shape of the annulus of the native tricuspid valve is not planar. For example, in some patients the native annulus is "saddle-shaped." Accordingly, in order to provide enhanced sealing between the valve 100 and the native annulus for such anatomies, in the depicted embodiment the main body 106 is made longitudinally longer (where the "length" aspect is defined along the axis 101) in certain areas to correspond with a non-planar saddle-shaped native annulus. In the depicted embodiment, as shown in FIGS. 4 and 5, there are at least two cells 102a and 102b (on the lateral and septal sides of the frame 102, so at least four cells in total) that extend farther into the right ventricle than the other cells of the frame 102. The end portion locations of those two cells 102a-b (on each side of the frame 102) correspond to the lower areas (toward the ventricle) of the saddle-shaped native annulus.

In some embodiments, the two cells 102a-b extend farther into the ventricle than any other portion of the valve 100. If the inflow end portion 102i is defined as the superior end of the valve 100 and the outflow end portion 1020 is defined as the inferior end of the valve 100, it can be said that the two cells 102a-b extend farther inferiorly than any other part of the valve 100 including, for example, the second portion 130b of the posterior flap 130.

Still referring to FIGS. 4-6, in the depicted embodiment, the valve 100 includes one or more optional suture knots 105. The suture knots 105 can be comprised of suture thread material (e.g., ligature thread material) that is bunched together in a knotted form. The suture knots 105 are located on the exterior surface of the covering 104. Accordingly, the suture knots 105 are small protrusions that provide supplemental migration resistance to help maintain the valve 100 in a desired position relative to the native anatomy (e.g., relative to the annulus of the native tricuspid valve).

In some embodiments, the suture knots 105 are made of the same suture thread material that is used to attach the covering 104 to the frame 102. Accordingly, as in the depicted embodiment, the suture knots 105 can be located along the elongate members of the frame 102. However, such placement of the suture knots 105 is optional. The suture knots 105 can be located anywhere on the valve 100, and in any desired numbers. In the depicted embodiment, the suture knots are located on the inferior lateral surfaces of the valve 100 (on the outflow end portion 1020) between the anterior flaps 120a-b and the posterior flap 130 of the valve 100. Alternatively or additionally, in some embodiments suture knots 105 can be located on other external surface areas of the valve 100.

As shown in FIG. 6, the depicted embodiment includes an opening 126a that is defined by the covering 104 located at a terminal end portion of the first anterior flap 120a. Additionally, the covering 104 on the second anterior flap 120b defines an opening 126b at a terminal end portion of the second anterior flap 120b.

The openings 126a-b in the end portions of the anterior flaps 120a-b allow blood to flow through the anterior flaps 120a-b (via the openings 126a-b). This can be beneficial because in some implementations the anterior flaps 120a-b extend into the RVOT. Accordingly, such openings 126a-b may in some cases reduce the potential of the anterior flaps 120a-b to restrict blood flow through the RVOT.

In the depicted embodiment, the posterior flap 130 includes a first portion 130a and a second portion 130b that are arranged at an angle in relation to each other. The first portion 130a extends away from the outflow end portion 1020 of the main body 106 generally transverse to the axis 101 of the occluder 110. The second portion 130b of the posterior flap 130 extends from the first portion 130a. In the depicted embodiment, the second portion 130b extends generally parallel to the axis 101 of the occluder 110. The angle defined between the first portion 130a and the second portion 130b can be in a range of 80° to 100°, or 70° to 110°, or 60° to 120°, or 50° to 130°, or 40° to 140°, without limitation.

The first anterior flap 120a and the second anterior flap 120b each extend in the same direction, which is opposite of the direction that the posterior flap 130 extends. In the depicted embodiment, portions of the first anterior flap 120a and the second anterior flap 120b overlap each other. An advantage of having the two separate anterior flaps 120a-b (rather than a single larger anterior flap) is that the anterior flap portion of the valve 100 can be radially compressed to a smaller profile for transcatheter delivery by the virtue of having the two separate anterior flaps 120a-b (as compared to having a single larger anterior flap).

In some embodiments, as shown in FIG. 5, the first and second anterior flaps 120a-b extend into the RVOT and overlap one axially on top of the other. This arrangement is functionally akin to a cantilevered beam arrangement. With the first and second anterior flaps 120*a-b* overlapping on each other, the bending resistance of the combination of the first and second anterior flaps 120*a-b* is increased (as compared to a single flap or non-overlapping flaps). This arrangement enables an advantageous extent of rigidity, without having to use framework members that are larger in cross-section. That is, the overlapping arrangement of the first and second anterior flaps 120*a-b* allow for the use of smaller framework members, which in turn importantly allows for a smaller collapsed delivery size (diameter). In other words, overlapping arrangement of the first and second anterior flaps 120*a-b* provides a support structure that is thicker without having to use a material with higher wall thickness (from which the framework is created); ultimately providing the bending stiffness or rigidity that keeps the valve 100 stable when RV pressure acts on the valve 100.

In the depicted embodiment, an open passage 122 is defined between the first anterior flap 120*a* and the second anterior flap 120*b*. The open passage 122 can be used, for example, for passing a pacemaker lead through the valve 100, without disturbing the functioning of the occluder 110. Accordingly, the valve 100 can facilitate the pass-through of the pacemaker lead while still providing sealing to prevent tricuspid valve regurgitation from the RV to the RA. In some cases, the pacemaker lead is pre-existing and the valve 100 is implanted subsequently (with the open passage 122 being used to receive the pacemaker lead). In other cases, the valve 100 can be pre-existing and the pacemaker lead can be subsequently passed through the open passage 122. This could take place both during the same implant procedure, or as a subsequent procedure.

Still referring to FIGS. 4-6, in some embodiments the valve 100 also includes one or more leaflet engagement members 140. In the depicted embodiment, the valve 100 includes two leaflet engagement members: a first leaflet engagement member 140*a* and a second engagement member 140*b*. In the depicted embodiment, the leaflet engagement members 140*a-b* extend from the outflow end portion 102*o* of the main body 106. In some embodiments, the leaflet engagement members 140*a-b* extend from the mid-body portion 102*m* of the main body 106.

The leaflet engagement members 140*a-b* extend from the frame 102 and bend toward the inflow end portion 102*i* of the main body 106. In other words, a portion of each leaflet engagement member 140*a-b* extends toward the inflow end portion 102*i* of the main body 106. A space, groove, or slot is defined between the leaflet engagement members 140*a-b* and the outer surface of the frame 102 (with the covering 104 being present on the frame 102 and leaflet engagement members 140*a-b*). As described further below, the space, groove, or slot receives and mechanically captures/holds a portion of a native leaflet (e.g., the posterior leaflet 11*p* and/or the septal leaflet 11*s*) to provide migration resistance for the valve 100.

In the depicted embodiment, the leaflet engagement members 140*a-b* extend from the frame 102 of the main body 106 in the same direction as the posterior flap 130. The posterior flap 130 extends away from the main body 106 farther than the leaflet engagement members 140*a-b*. Various other arrangements of the leaflet engagement members 140*a-b* and the posterior flap 130 are also envisioned and within the scope of this disclosure.

The leaflet engagement members 140*a-b* may be U-shaped wire loops, as in the depicted embodiment. The wire loops that make up the leaflet engagement members 140*a-b* can be continuous with the wire members of the frame 102.

In the depicted embodiment, the leaflet engagement members 140*a-b* terminate at free ends. Accordingly, the leaflet engagement members 140*a-b* point toward the inflow end portion 102*i* of the main body 106, with the free ends of the leaflet engagement members 140*a-b* being the closest to the inflow end portion 102*i*. This arrangement defines the space, groove, or slot receives and mechanically captures/holds a portion of a native leaflet to provide migration resistance for the valve 100.

The depicted embodiment of the valve 100 includes an optional posterior arm 150. The posterior arm 150 comprises a wire member (e.g., an elongated loop) that extends from the frame 102 and includes a free end 150*e* (which can also be said to be located at a distal end portion of the posterior arm 150). In some embodiments, the posterior arm 150 is a wire member that is constructed unitarily with wire members of the frame 120. Hence, it can be said that the posterior arm 150 is a portion of the frame 120. In the depicted embodiment, the covering 104 is attached to the posterior arm 150, including the free end 150*e*.

In the depicted embodiment, the posterior arm 150 extends from the inflow end portion 102*i* of the frame 102. The posterior arm 150 extends in a direction that is the same as, or that is generally (e.g., +/−20°) parallel to, the direction in which the posterior flap 130 extends. In some embodiments, the posterior arm 150 extends from the mid-body portion 102*m* of the frame 102. The location of the free end 150*e* is within a transverse plane (e.g., taken perpendicular to the axis 101) that intersects the mid-body portion 102*m* of the frame 102 or the inflow end portion 102*i* of the frame 102.

The posterior arm 150 provides additional anchorage and migration resistance for the valve 100. As depicted in FIG. 5, the free end 150*e* of the posterior arm 150 abuts against an anatomical structure when the valve 100 is engaged in a native tricuspid valve 10. In some cases, the free end 150*e* of the posterior arm 150 abuts against an interior wall of an inferior vena cava, or coronary sinus, or the right atrium, or another anatomical structure. Where it abuts can be largely a function of the variable anatomy from patient to patient. The migration resistance provided by the posterior arm 150 can be particularly advantageous during diastole when the occluder 110 is open to allow blood flow from the right atrium to the right ventricle via the occluder 110.

Referring also to FIG. 7, in some embodiments the frame 102 can include an anterior arm 160. The anterior arm 160 may also be covered similarly to the posterior arm 150. The anterior arm 160 comprises a wire member (e.g., an elongated loop) that extends from the frame 102 and includes a free end 160*e* (which can also be said to be located at a distal end portion of the posterior arm 160). In some embodiments, the anterior arm 160 is a wire member that is constructed unitarily with wire members of the frame 120. Hence, it can be said that the anterior arm 160 is a portion of the frame 120. In the depicted embodiment, the covering 104 is attached to the anterior arm 160, including the free end 160*e*.

In the depicted embodiment, the anterior arm 160 extends from the inflow end portion 102*i* of the frame 102. The anterior arm 160 extends in an anterior direction away from the axis 101 (e.g., a direction that is generally the same as the direction in which the anterior flaps 120*a-b* extend). In some embodiments, the anterior arm 160 extends from the mid-body portion 102*m* of the frame 102. The location of the free end 160*e* is within a transverse plane (e.g., taken perpendicular to the axis 101) that intersects the mid-body portion 102*m* of the frame 102 or the inflow end portion 102*i* of the frame 102.

The anterior arm 160 provides additional anchorage and migration resistance for the valve 100. The free end 160e of the anterior arm 160 abuts against an anatomical structure when the valve 100 is engaged in a native tricuspid valve 10. In some cases, the free end 160e of the anterior arm 160 abuts against an interior wall of a right atrial appendage or another anatomical structure. Where the anterior arm 160 lands relative to the anatomy can vary based on patient to patient variability. The migration resistance provided by the anterior arm 160 can be particularly advantageous during diastole when the occluder 110 is open to allow blood flow from the right atrium to the right ventricle via the occluder 110.

Some embodiments of the valve 100 include the posterior arm 150, but not the anterior arm 160. Other embodiments of the valve 100 include the anterior arm 160, but not the posterior arm 150. Still other embodiments of the valve 100 include both the posterior arm 150 and the anterior arm 160.

In some embodiments, such as the depicted embodiment (e.g., as best visible in FIG. 7), the septal and lateral edge portions of the anterior flaps 120a-b can include a strut framework to provide additional structural sturdiness to the anterior flaps 120a-b. In particular, the first anterior flap 120a includes a septal anterior strut framework 128a, and the second anterior flap 120b includes a lateral anterior strut framework 128b. As depicted in FIG. 7, in some embodiments the strut members of the septal anterior strut framework 128a can be "S-shaped," and the strut members of the lateral anterior strut framework 128b can be "L-shaped." This distinction between the septal anterior strut framework 128a and the lateral anterior strut framework 128b can provide the clinician with a visual indication of the orientation of the valve 100 while various visualization modalities (e.g., x-ray fluoroscopy) is/are being used during the deployment of the valve 100.

FIGS. 8 and 9 illustrate more details of the example prosthetic heart valve deployment system 200 (or "valve deployment system 200" or simply "deployment system 200"). The deployment system 200 includes the control handle 210, an outer sheath catheter 220, a middle deflectable catheter 230, and an inner control catheter 240. The outer sheath catheter 220 defines a first lumen. The middle deflectable catheter 230 is slidably disposed in the first lumen and defines a second lumen. The inner control catheter 240 is slidably disposed in the second lumen. A clinician user can control the positions, relative to each other, of the outer sheath catheter 220, the middle deflectable catheter 230, and the inner control catheter 240 by manipulating the control handle 210.

In some embodiments, the outer sheath catheter 220 is selectively deflectable or steerable. That is, in some embodiments a clinician can controllably steer or deflect a distal end portion of the outer sheath catheter 220 during the deployment process of the valve 100. This steerability of the outer sheath catheter 220 can be beneficial to the clinician when navigating the patient's anatomy and/or during the actual valve release or retrieval processes in the patient's heart.

Figure 11:
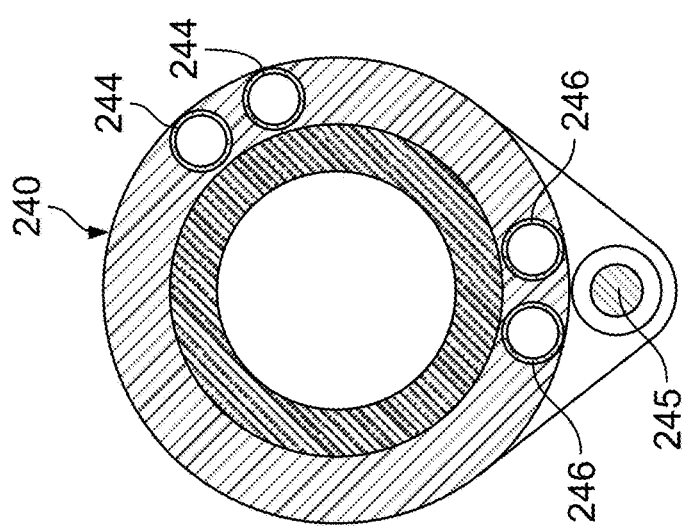
FIG. 11 is a second cross-sectional view of the control catheter of the transcatheter prosthetic heart valve deployment system of FIG. 8.

The inner control catheter 240 includes a curved portion 242. The curved portion 242 is elastically deformable. That is, while the curved portion 242 is located within the confines of the first lumen of the outer sheath catheter 220, the curved portion 242 is essentially linear (or at least more linear than when the curved portion 242 is radially unconstrained). When the curved portion 242 of the inner control catheter 240 is distally expressed out (either by pushing the inner control catheter 240 distally or by pulling the outer sheath catheter 220 proximally) from the confines of the first lumen of the outer sheath catheter 220, the curved portion 242 then naturally elastically reconfigures to exhibit a pronounced curve (e.g., as shown in FIG. 11). Thus, it can be said that the natural shape, or unconstrained shape, of the inner control catheter 240 includes the curved portion 242 that defines an interior angle. In some embodiments, the interior angle can be between 130° and 160°, or between 120° and 150°, or between 110° and 140°, or between 100° and 130°, or between 90° and 120°, or between 80° and 110°, or between 80° and 100°, without limitation. In some embodiments, the interior angle can be less than 160°, or less than 150°, or less than 140°, or less than 135°, or less than 130°, or less than 120°, or less than 110°, or less than 100°, or less than 90° without limitation.

The middle deflectable catheter 230 includes a selectively deflectable distal end portion with at least one plane of deflection. In some embodiments, the selectively deflectable distal end portion is deflectable in two planes. In some embodiments, the middle deflectable catheter 230 includes two or more separate selectively deflectable portions that are in same planes or in different planes. A clinician user can control the extent of deflection of the selectively deflectable distal end portion of the middle deflectable catheter 230 by manipulating an actuator of the control handle 210.

In the depicted embodiment, the selectively deflectable distal end portion can be selectively deflectable in a same plane as the plane of the curved portion 242 of the inner control catheter 240. Accordingly, when the selectively deflectable distal end portion of the middle deflectable catheter 230 is deflected by a clinician user, the curvature of the combination of the middle deflectable catheter 230 and the inner control catheter 240 in relation to the axis of the outer sheath catheter 220 is increased beyond that of the interior angle of the inner control catheter 240 alone. In some embodiments, the combined curvature of the middle deflectable catheter 230 and the inner control catheter 240 in relation to the axis of the outer sheath catheter 220 can define an interior angle between 90° and 110°, or between 80° and 100°, or between 70° and 90°, or between 60° and 80°, or between 50° and 70°, or between 30° and 60°, or between 0° and 30°, without limitation. This high degree of curvature can be beneficial during deployment of a prosthetic valve (such as the valve 100) using the deployment system 200, as described further below.

The inner control catheter 240 can also include mechanical features for releasably coupling with a prosthetic valve (such as, but not limited to, the valve 100; see FIGS. 4-7). For example, in the depicted embodiment, the inner control catheter 240 includes one or more control wires and/or release pins that can releasably couple a prosthetic valve (e.g., the valve 100) to the inner control catheter 240 in a low profile delivery configuration for transcatheter, trans-vascular deployment at a native heart valve location of a patient.

In the depicted embodiment (e.g., as seen in FIG. 9), the valve deployment system 200 includes a first control wire 243, a second control wire 244, a third control wire 245, a fourth control wire 246, and a fifth control wire 247. The control wires 243, 244, 245, 246, and 247 are each individually controllable by a clinician user at the control handle 210 (as described further below).

The control wires 243, 244, and 246 are each wire loops. That is, each of the control wires 243, 244, and 246 has two free ends that are located at the control handle 210. The control wires 243, 244, and 246 each extend continuously between their two free ends, thereby forming the loops as shown in FIG. 9. The loops releasably couple with particular portions of the prosthetic heart valve, as described further below (e.g., FIGS. 13 and 14).

When a clinician user applies tension to the looped control wires 243, 244, and 246 at the control handle 210, the respective wire loop (and the respective portions of the prosthetic heart valve to which the control wires 243, 244, and 246 are coupled) are drawn radially closer to the inner control catheter 240. When a clinician user relaxes the tension of the control wires 243, 244, and 246 (e.g., individually distally feeds out or pays out the control wires 243, 244, and 246) the respective portions of the prosthetic heart valve to which the control wires 243, 244, and 246 are each coupled are allowed to radially self-expand away from the inner control catheter 240.

A clinician user can fully uncouple the looped control wires 243, 244, and 246 from the prosthetic heart valve by proximally pulling one free end portion of the respective looped control wire 243, 244, or 246 (and continuing such proximal pulling) until the other free end portion is fully pulled out of engagement with the prosthetic heart valve.

In contrast to the looped control wires 243, 244, and 246, the control wires 245 and 247 (which can also be referred to as "release pins") do not comprise wire loops. Instead, the control wires 245 and 247 each have a first free end at the control handle 210 and a second free end that distally terminates at a respective location at the distal end portion of the deployment system 200.

Like the looped control wires 243, 244, and 246, the control wires 245 and 247 are each coupled with a particular portion of the prosthetic heart valve. For example, at the distal end portion of the deployment system 200, the third control wire 245 is coupled with a portion of the prosthetic heart valve (as described in reference to FIGS. 13 and 14). The third control wire 245 then releasably terminates at the distal tip member 241 of the inner catheter 240. Similarly, the fifth control wire 247, at the distal end portion of the deployment system 200, is coupled with a portion of the prosthetic heart valve (as described in reference to FIGS. 13 and 14). The fifth control wire 247 then releasably terminates at a distal collar 231 of the deflectable catheter 230.

When the control wires 245 and 247 are pulled proximally (individually), their respective distally-located free ends uncouple from the distal tip member 241 or the distal collar 231, respectively. In addition, when the control wires 245 and 247 are pulled proximally (individually), the respective portion of the prosthetic heart valve to which the control wires 245 and 247 are releasably coupled are released from their detainment by the control wires 245 and 247 and are allowed to self-expand to their natural configuration.

Figure 12:
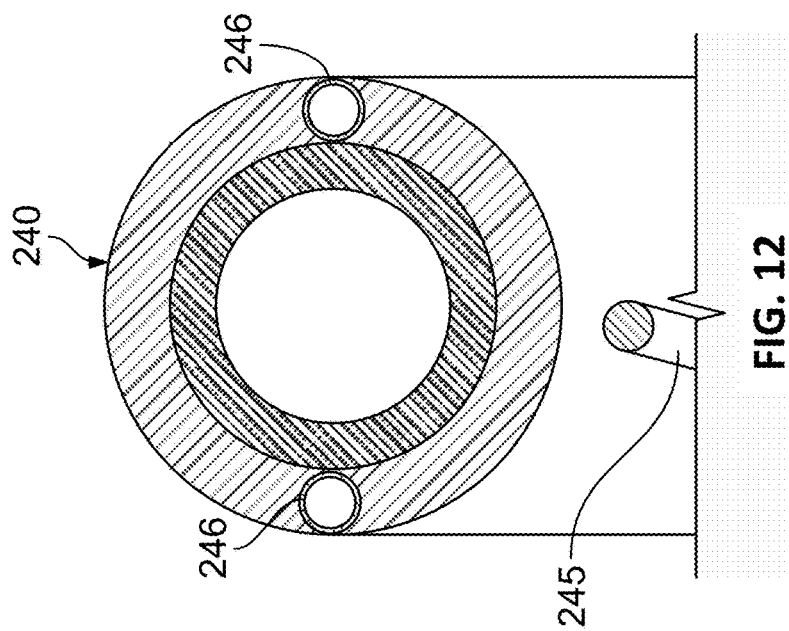
FIG. 12 is a third cross-sectional view of the control catheter of the transcatheter prosthetic heart valve deployment system of FIG. 8.
Figure 10:
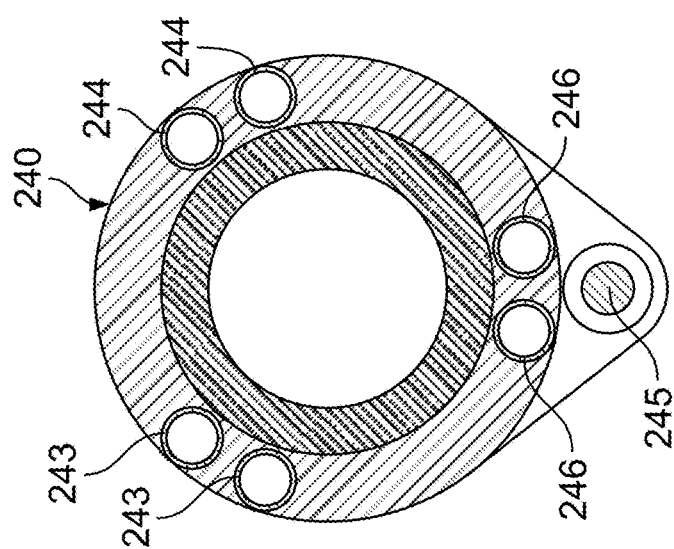
FIG. 10 is a first cross-sectional view of a control catheter of the transcatheter prosthetic heart valve deployment system of FIG. 8.

As shown in the various cross-sectional views of the inner catheter 240 in FIGS. 10-12, the control wires 243, 244, 245, and 246 are each slidably disposed in lumens defined by the wall of the inner catheter 240. FIG. 10 is taken at the cut plane 12-12 shown in FIG. 9. Accordingly, FIG. 10 shows each of the control wires 243, 244, 245, and 246. Shortly after the cut plane 12-12 (moving distally), the first control wire 243 exits the lumens of the inner catheter 240 to form the loop shown in FIG. 9. Accordingly, in FIG. 11 (taken at the cut plane 13-13 of FIG. 9) the first control wire 243 is no longer seen. Instead, only the control wires 244, 245, and 246 are seen. Shortly after the cut plane 13-13 (moving distally), the second control wire 244 exits the lumens of the inner catheter 240 to form the loop shown in FIG. 9. Accordingly, in FIG. 12 (taken at the cut plane 14-14 of FIG. 9) the second control wire 244 is no longer seen. Instead, only the control wires 245 and 246 are seen. Shortly after the cut plane 14-14 (moving distally), the fourth control wire 246 exits the lumens of the inner catheter 240 to form the loop shown in FIG. 9. The third control wire 245 continues distally and terminates at the distal tip member 241 of the inner catheter 240. The fifth control wire 247 is not seen in FIGS. 10-12 because it distally terminates at the distal collar 231 of the deflectable catheter 230 (prior to the proximal-most cut plane 12-12).

Figure 13:
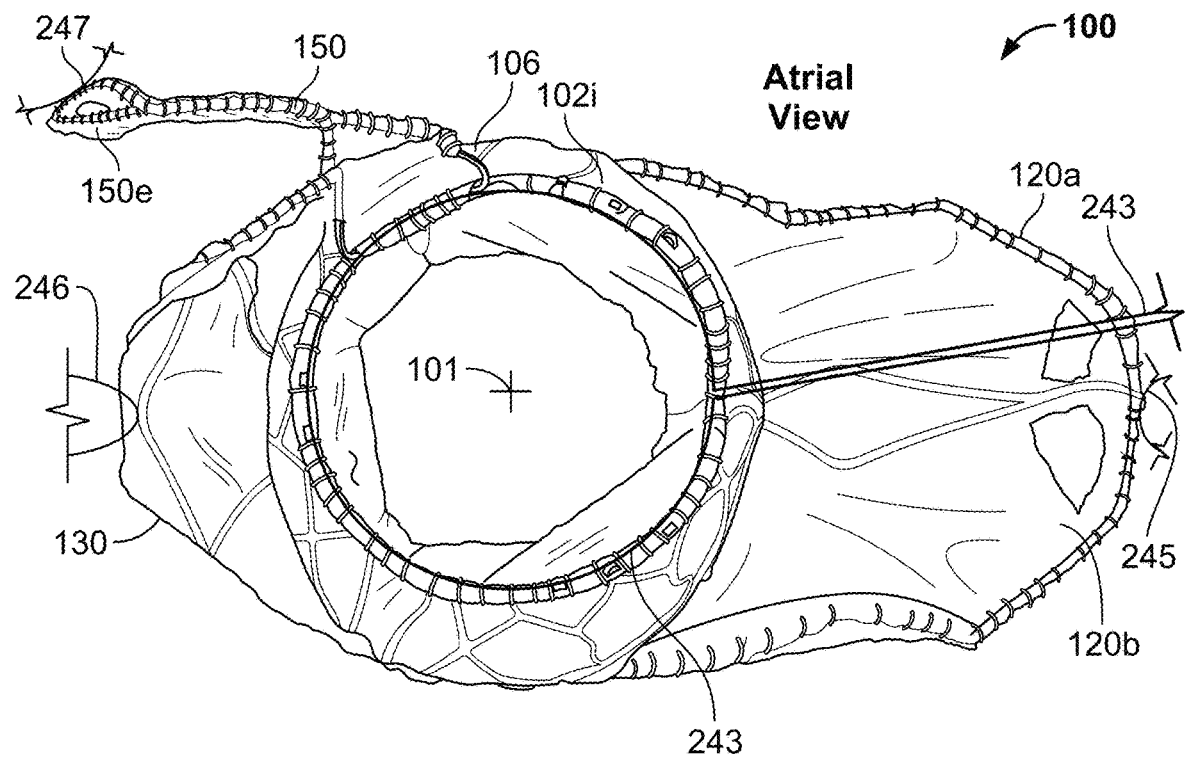
FIG. 13 shows a top or atrial view of an example prosthetic heart valve including indications of example locations to which control wires are releasably coupled for deploying the prosthetic valve using the transcatheter prosthetic heart valve deployment systems described herein.
Figure 14:
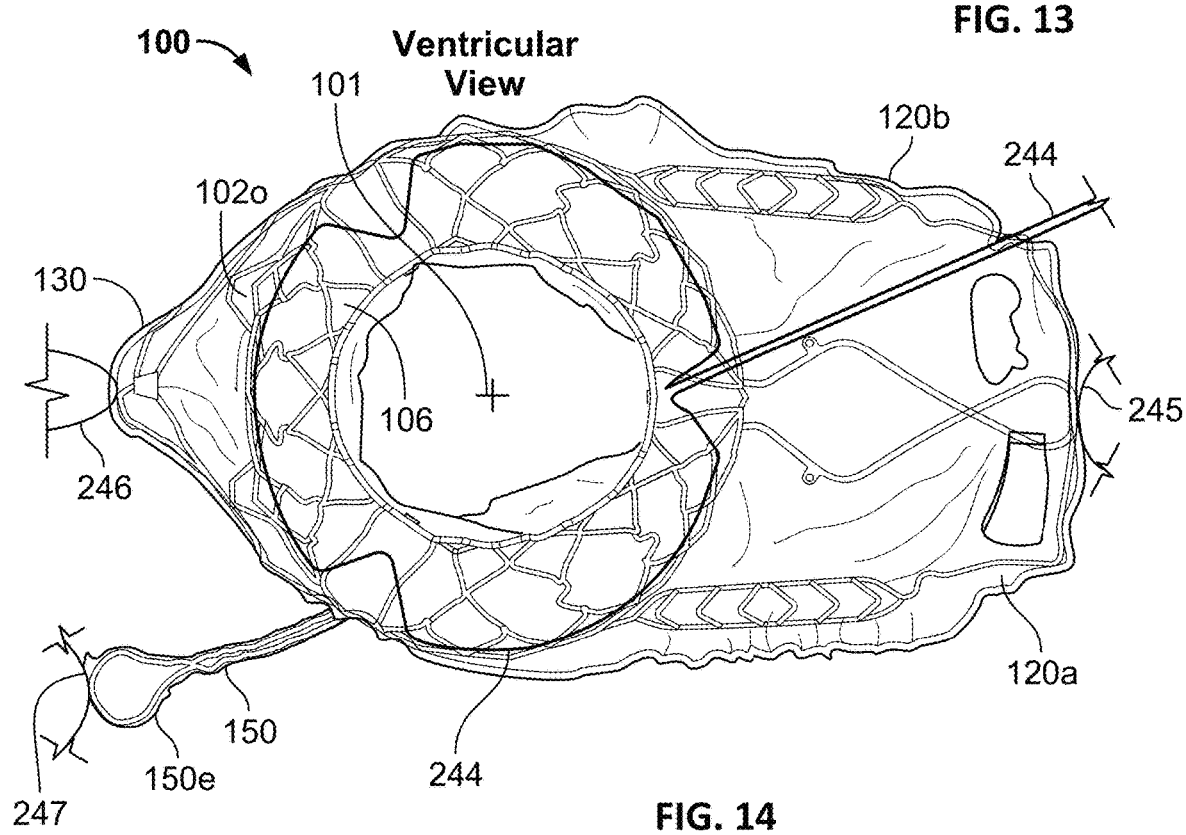
FIG. 14 shows a bottom or ventricular view of the example prosthetic heart valve of FIG. 13, including indications of example locations to which control wires are releasably coupled for deploying the prosthetic valve using the transcatheter prosthetic heart valve deployment systems described herein.

FIGS. 13 and 14 illustrate how the control wires 243, 244, 245, 246, and 247 can be releasably coupled to respective portions of the prosthetic heart valve 100. In some embodiments, the control wires 243, 244, 245, 246, and 247 are releasably coupled with the wire elements of the frame 102. In some embodiments, an additional member (such as a suture loop, a ring, etc.) is used to releasably couple one or more of the control wires 243, 244, 245, 246, and 247 to the particular portions of the prosthetic heart valve 100.

As shown in FIG. 13, the first control wire 243 can be releasably coupled to the inflow end 102i of the main body 106. In particular, the first control wire 243 can be arranged in a loop and releasably coupled around the perimeter of the inflow end 102i. When tensioned, the first control wire 243 can cinch the inflow end 102i radially inward toward the inner control catheter 240 like a lasso or a purse string.

As shown in FIG. 14, the second control wire 244 can be releasably coupled to the outflow end 102o of the main body 106. In particular, the second control wire 244 can be arranged in a loop and releasably coupled around the perimeter of the outflow end 102o. When tensioned, the second control wire 244 can cinch the outflow end 102o radially inward toward the inner control catheter 240 like a lasso or a purse string.

The third control wire 245 is configured as a release pin that can be releasably coupled to the anterior flap 120a and/or the anterior flap 120b of the prosthetic heart valve 100. The third control wire 245 simply extends through the anterior flap 120a and/or the anterior flap 120b and then releasably terminates at the distal tip member 241. The third control wire 245 is held closely adjacent to the distal tip member 241 by the structure of the distal tip member 241. The third control wire 245 thereby holds the anterior flap 120a and/or the anterior flap 120b close to the distal tip member 241.

The fourth control wire 246 is a wire loop that can be releasably coupled to the posterior flap 130. When tensioned, the fourth control wire 246 can pull the posterior flap 130 radially inward toward the inner control catheter 240 like a snare.

The fifth control wire 247 is configured as a release pin that can be releasably coupled to the posterior arm 150 of the prosthetic heart valve 100. For example, the fifth control wire 247 can simply extend through the free end 150e of the posterior arm 150 and then releasably terminate at the distal collar 231 of the middle deflectable catheter 230. The tension of the fifth control wire 247 holds the fifth control wire 247 closely adjacent to the middle deflectable catheter 230. The fifth control wire 247 thereby holds the posterior arm 150 close to the middle deflectable catheter 230 while the fifth control wire 247 is in tension.

Figure 15:
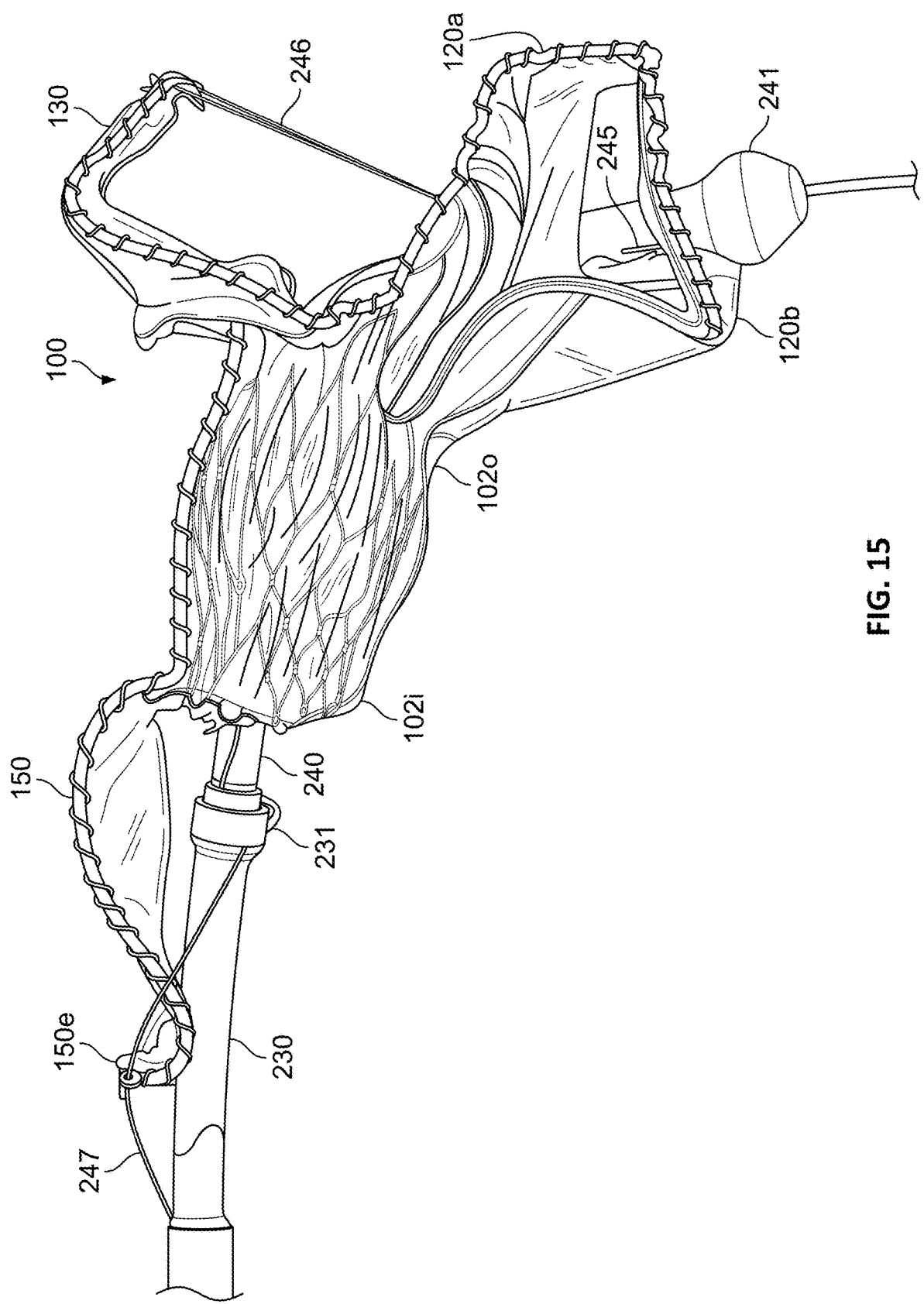
FIG. 15 shows an example prosthetic heart valve that is releasably coupled by control wires to a distal end portion of an example transcatheter prosthetic heart valve deployment system described herein.

FIG. 15 shows the prosthetic heart valve 100 releasably coupled to the middle deflectable catheter 230 and the inner control catheter 240 by the control wires 243, 244, 245, 246, and 247 (in this view the control wires 243 and 244 are not visible). The posterior flap 130 is shown in a partially expanded orientation (e.g., with the tension of the fourth control wire 246 partially relaxed). During the initial delivery process of the prosthetic heart valve 100 the posterior flap 130 would be drawn in and held more closely radially inward to the inner catheter 240 than the depicted orientation.

Figure 17:
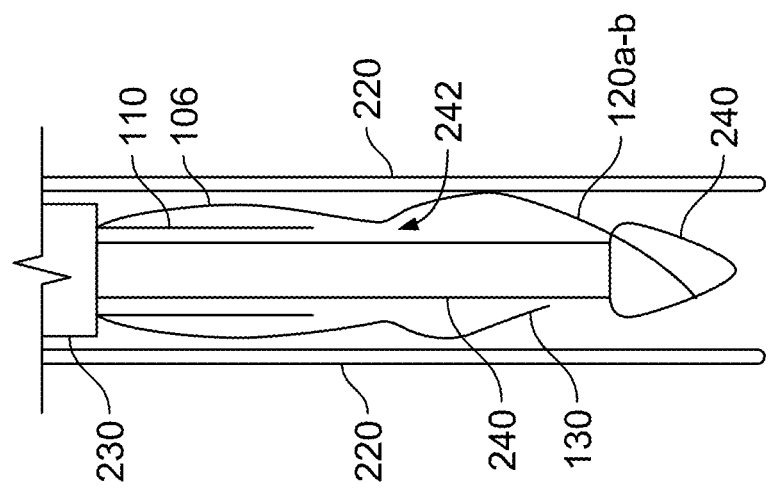
FIG. 17 schematically shows the prosthetic tricuspid valve of FIG. 16 coupled with the prosthetic heart valve deployment system of FIG. 10.
Figure 16:
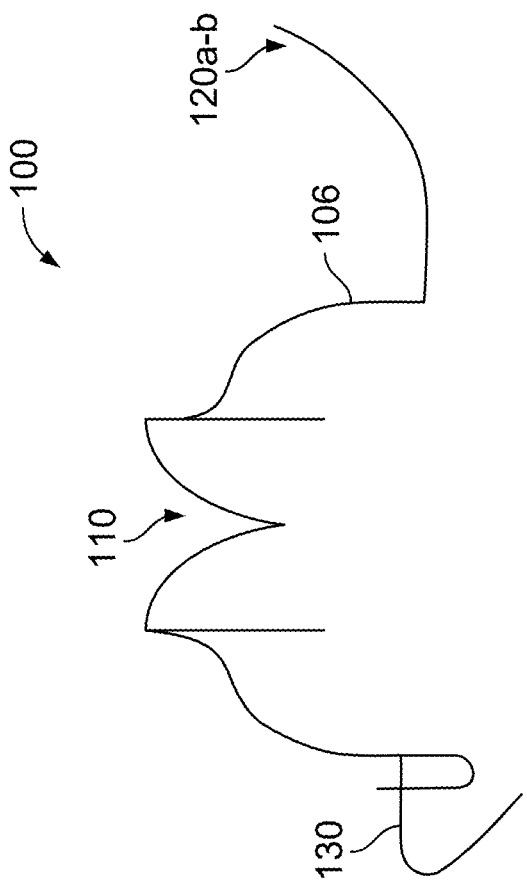
FIG. 16 schematically illustrates a side view of the prosthetic tricuspid valves described herein.

FIG. 16 shows a schematic illustration of the valve 100. FIG. 17 schematically shows the valve 100 coupled to the inner control catheter 240 and located within the first lumen defined by the outer sheath catheter 220. The distal tip of the middle deflectable catheter 230 is also visible. In this arrangement, the valve 100 is radially compressed to a low-profile delivery configuration while within the outer sheath catheter 220. In some embodiments, the valve 100 (or portions thereof are wrapped or folded around the inner control catheter 240. For example, in some embodiments the anterior flaps 120a-b are wrapped around the inner control catheter 240. The valve 100 can tend to try to self-expand as it emerges from the outer sheath catheter 220 (e.g., by the manual retraction of the outer sheath catheter 220 relative to the middle deflectable catheter 230 and the inner control catheter 240). However, during the deployment process, the clinician user can controllably expand and/or release the particular portions of the valve 100 to which the control wires 243, 244, 245, 246, and 247 are releasably coupled.

In some embodiments, when the valve 100 is in its collapsed delivery configuration within the outer sheath catheter 220, the portions of the valve 100 are arranged relative to each other as follows. The first and second anterior flaps 120a-b (which can be wrapped on each other) are distal-most. The posterior arm 150 is proximal-most within the outer sheath catheter 220. The occluder portion (or valve core) 110 with the flexible leaflets is the next proximal-most. The posterior anchoring flap 130 is arranged between the distal-most first and second anterior flaps 120a-b and the occluder portion 110.

The control wires 243, 244, 245, 246, and 247 can be tensioned to draw and maintain the associated portions of the valve 100 radially inward to be snug against the inner control catheter 240. During deployment of the valve 100, the control wires 243, 244, 245, 246, and 247 can be individually relaxed and then released to allow the associated portion of the valve 100 to expand elastically toward its natural expanded shape.

Still referring to FIG. 17, in this delivery configuration the curved portion 242 of the inner control catheter 240 is being constrained in an essentially linear configuration by the outer sheath catheter 220. However, when the inner control catheter 240 is expressed from the outer sheath catheter 220 (or as the outer sheath catheter 220 is pulled proximally relative to the inner control catheter 240), the curved portion 242 will become unconstrained and will elastically deflect to its natural curved configuration (e.g., as shown in FIG. 15). The curved configuration of the curved portion 242 is beneficial for the deployment process of the valve 100 into engagement with a native tricuspid valve 10, as described further below.

Figure 18:
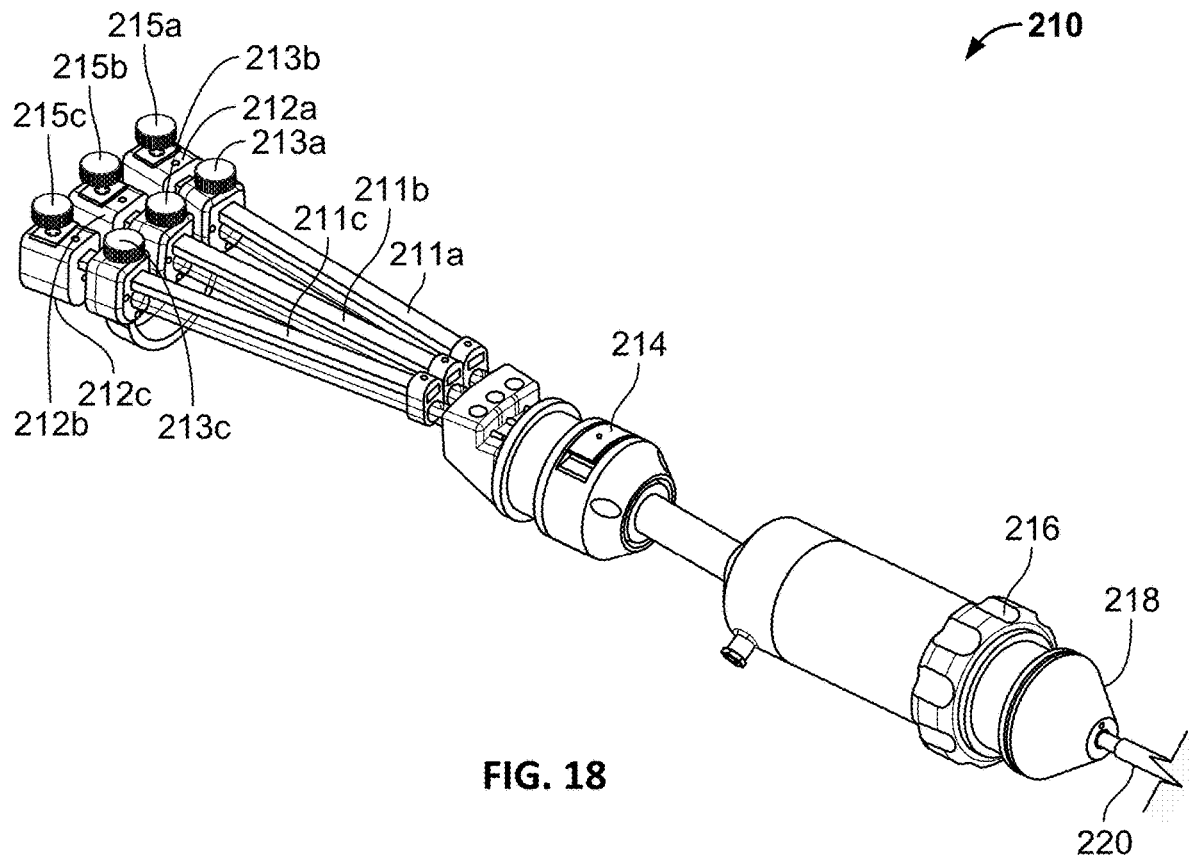
FIG. 18 shows a perspective view of an example control handle of a transcatheter prosthetic heart valve deployment system in accordance with some embodiments.

FIG. 18 shows the control handle 210 in more detail. The control handle 210 includes: (i) a first control wire tension adjustment mechanism 211a and 212a (which is used by a clinician user to control the tension of the first control wire 243), (ii) a second control wire tension adjustment mechanism 211b and 212b (which is used by the clinician user to control the tension of the second control wire 244), and (iii) a third control wire tension adjustment mechanism 211c and 212c (which is used by the clinician user to control the tension of the fourth control wire 246).

The control handle 210 also includes a first control wire release handle 214 (which is used by the clinician user to pull the third control wire 245 proximally to release the one or more anterior flaps 120a/b). The first control wire release handle 214 is fixedly attached to the proximal free end of the third control wire 245 and releasably attached to the control handle 210. To pull the third control wire 245 proximally to release the one or more anterior flaps 120a/b, the first control wire release handle 214 can be detached from the control handle 210 and then used to pull the third control wire 245 proximally.

The control handle 210 also includes a steering actuator 216 (which is used by the clinician user to selectively deflect or steer the deflectable distal end portion 232 of the deflectable catheter 230).

The control handle 210 also includes a second control wire release handle 218 (which is used by the clinician user to pull the fifth control wire 247 proximally to release the posterior arm 150). The second control wire release handle 218 is fixedly attached to the proximal free end of the fifth control wire 247 and releasably attached to the control handle 210. To pull the fifth control wire 247 proximally to release the posterior arm 150, the second control wire release handle 218 can be detached from the control handle 210 and then used to pull the fifth control wire 247 proximally.

Figure 19:
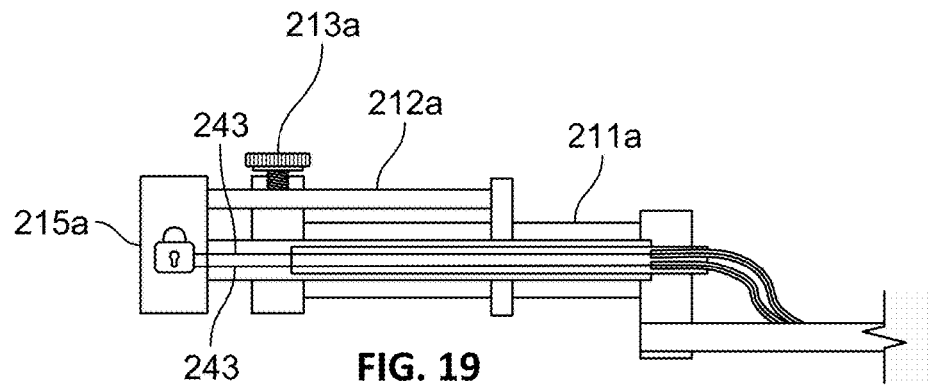
FIG. 19 schematically shows the control handle of FIG. 18 in a first orientation.
Figure 20:
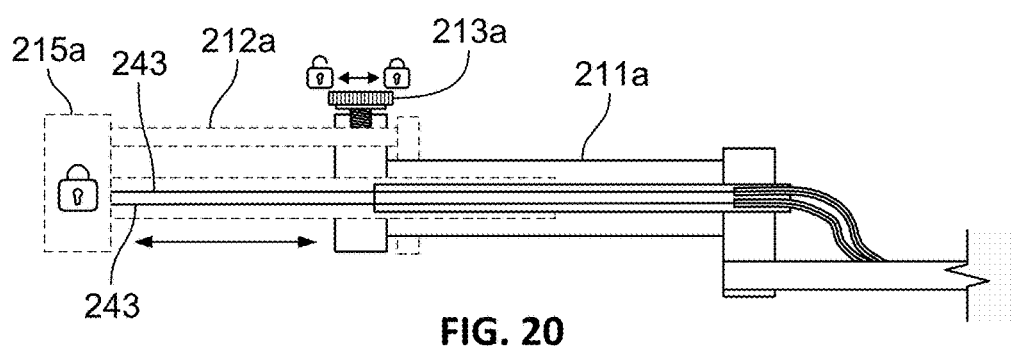
FIG. 20 schematically shows the control handle of FIG. 18 in a second orientation.

FIGS. 19 and 20 illustrate the manner in which the three control wire tension adjustment mechanisms of the control handle 210 can be individually manipulated by the clinician user to control the tension and release of the control wires 243, 244, and 246 that are configured in loops. The first control wire tension adjustment mechanism 211a and 212a, and the first control wire 243 are used in the depicted example. The other two control wire tension adjustment mechanisms can be operated in the same manner A comparison of FIG. 19 and FIG. 20 reveals that the mechanism 212a can be adjustably moved proximally and distally relative to the mechanism 211a. The two free ends of the control wire 243 are releasably attached to the mechanism 212a. The control wire 243 is slidable relative to the mechanism 211a. Therefore, the clinician user can add tension to the control wire 243 by proximally pulling the mechanism 212a relative to the mechanism 211a (e.g., as shown in FIG. 20). Conversely, the clinician user can relieve tension from the control wire 243 by distally pushing the mechanism 212a relative to the mechanism 211a (e.g., as shown in FIG. 19).

During the initial stages of the delivery of the prosthetic heart valve 100, the three control wire tension adjustment mechanisms of the control handle 210 will be arranged so as to apply tension to the control wires 243, 244, and 246. That is, the three control wire tension adjustment mechanisms of the control handle 210 will be oriented as shown in FIG. 20. Then, in a controlled manner during the delivery/deployment process, the clinician user can individually manipulate the three control wire tension adjustment mechanisms of the control handle 210 to allow the corresponding portions of the prosthetic heart valve 100 to expand, and then to be released from the corresponding control wire 243, 244, or 246.

The control handle 210 also includes a first latch mechanism 213a, a second latch mechanism 213b, and a third latch mechanism 213c. These latch mechanisms 213a-b are used by the clinician user to releasably detain the mechanisms 212a-c in the desired proximal/distal position relative to their corresponding mechanism 211a-c. The latch mechanisms 213a-b can be deactivated when the clinician user wants to make adjustments to the position of the mechanisms 212a-c relative to their corresponding mechanism 211a-c. Then, after making such adjustment(s), the clinician user can reactivate the latch mechanisms 213a-b to once again detain the mechanisms 212a-c relative to their corresponding mechanism 211a-c. In the depicted embodiment, the latch mechanisms 213a-b are set screws. In some embodiments, the latch mechanisms 213a-b can comprise various other mechanisms such as, but not limited to, spring-loaded pins, lock collars, collets, and the like.

The control handle 210 also includes a first control wire fastening mechanism 215a, a second control wire fastening mechanism 215b, and a third control wire fastening mechanism 215c. These control wire fastening mechanisms 215a-c are used to lock the control wires 243, 244, and 246 relative to their corresponding mechanism 212a-c. When the control wires 243, 244, and 246 are locked relative to the mechanisms 212a-c, the control wires 243, 244, and 246 will be tensioned when the mechanisms 212a-c are pulled proximally relative to their corresponding mechanism 211a-c. For example (referring to the example depicted by FIGS. 19 and 20), when the first control wire fastening mechanism 215a is activated to lock the first control wire 243 relative to the mechanism 212a, moving the mechanism 212a proximally relative to its corresponding mechanism 211a will add tension to the first control wire 243. Accordingly, the first control wire 243 will have a higher tension in the arrangement of FIG. 20 as compared to the arrangement of FIG. 19. In this manner (and referring to FIG. 15, for example), the clinician user can control the tension of the control wires 243, 244, and 246, which results in controlling the expansion/contraction of the inflow end portion 102i, the outflow end portion 102o, and the posterior flap 130 respectively.

The control wire fastening mechanisms 215a-c are also activated by the clinician user when the clinician user wants to fully release the control wires 243, 244, or 246 from being engaged with their corresponding portions of the prosthetic heart valve 100 in order to fully deploy the corresponding portions of the prosthetic heart valve 100. For example (and referring to FIG. 15, for example), when the clinician user wants to fully release the posterior flap 130 to its fully deployed position, the clinician user can unlock the fourth control wire 246 from its control wire fastening mechanisms 215a-c and then proximally pull on one free end of the fourth control wire 246 until the fourth control wire 246 becomes fully uncoupled from the posterior flap 130 as a result of the other free end of the fourth control wire 246 being pulled through and then away from the posterior flap 130. In the depicted embodiment, the control wire fastening mechanisms 215a-b are set screws. In some embodiments, the control wire fastening mechanisms 215a-b can comprise various other mechanisms such as, but not limited to, over-center clamps, lock collars, collets, and the like.

Figure 21:
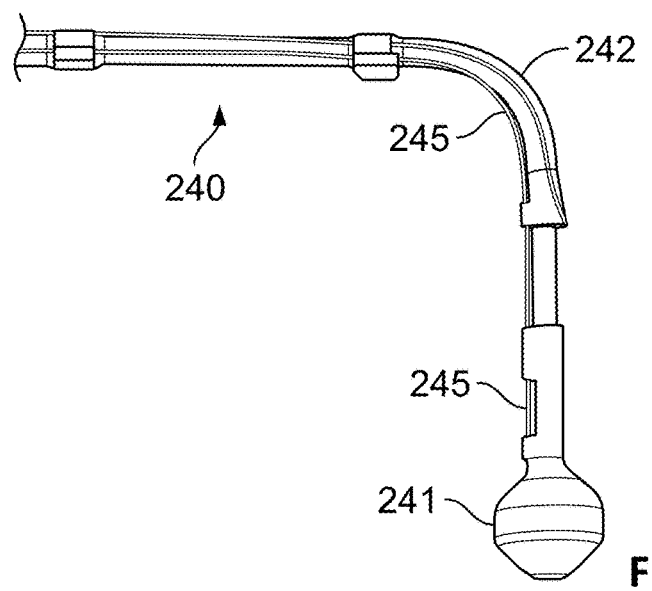
FIGS. 21-23 show various orientations of an example control wire that is coupled to a distal end portion of a control catheter of the prosthetic heart valve deployment system of FIG. 8.
Figure 22:
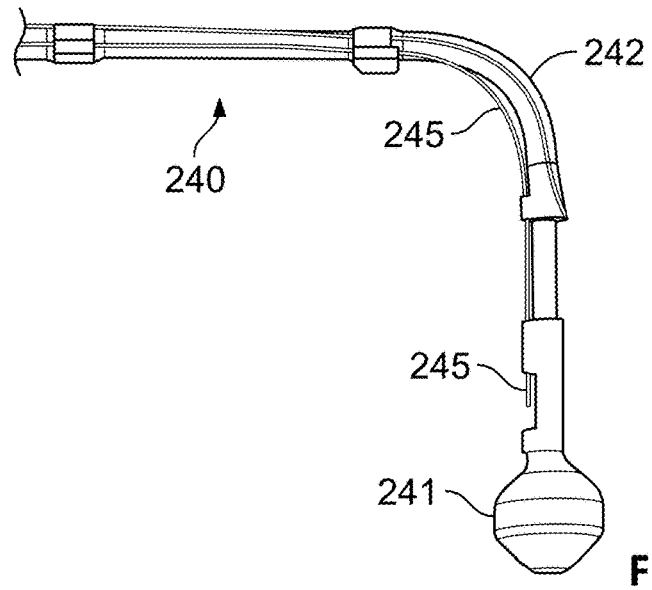
Figure 23:
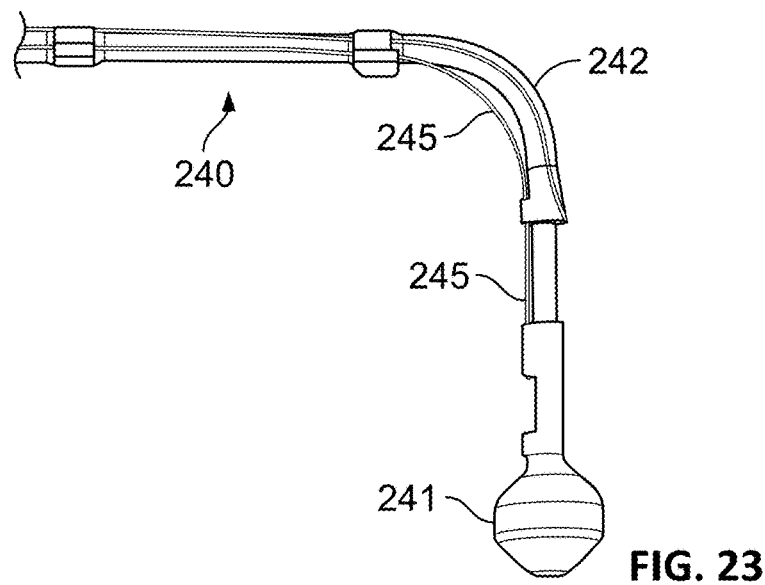

The control handle 210 also includes the first control wire release handle 214 that is used by the clinician user to pull the third control wire 245 proximally to release/deploy the one or more anterior flaps 120a/b of the prosthetic heart valve 100. FIGS. 21-23 sequentially illustrate the movements of the distal end portion of the third control wire 245 as the clinician user proximally pulls the third control wire 245 using the first control wire release handle 214. FIG. 21 shows the distal end portion of the third control wire 245 in its initial position in which it is fully engaged with the distal tip member 241. In this position, the third control wire 245 holds the one or more anterior flaps 120a/b adjacent to the inner control catheter 240 in their low-profile delivery configuration (e.g., as shown in FIG. 15). FIG. 22 shows the third control wire 245 in the process of being disengaged from the distal tip member 241. FIG. 23 shows the third control wire 245 fully disengaged from the distal tip member 241. In this arrangement, the one or more anterior flaps 120a/b are released by the third control wire 245 to expand to their fully deployed configurations.

Figure 24:
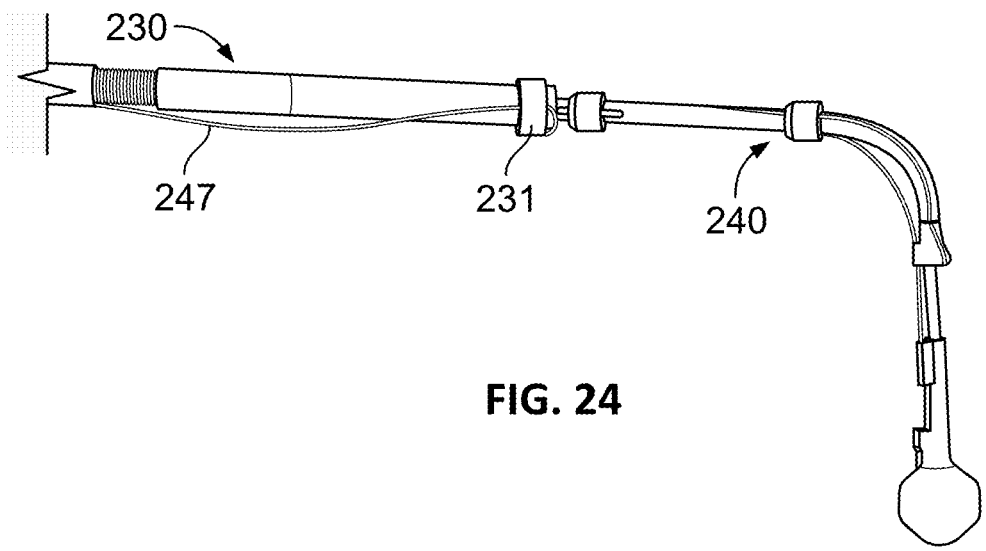
FIGS. 24-26 show various orientations of another example control wire that is coupled to a distal end portion of a control catheter of the prosthetic heart valve deployment system of FIG. 8.
Figure 25:
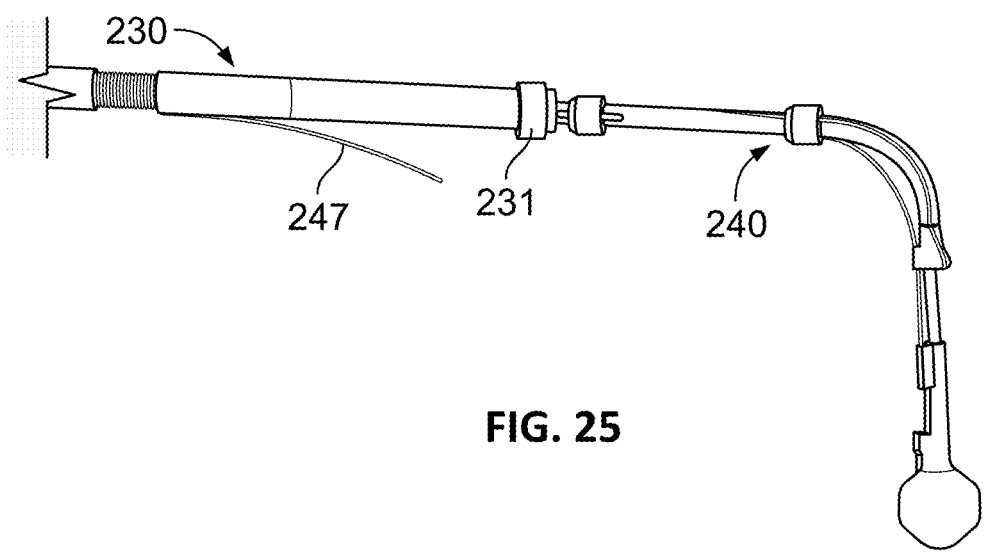
Figure 26:
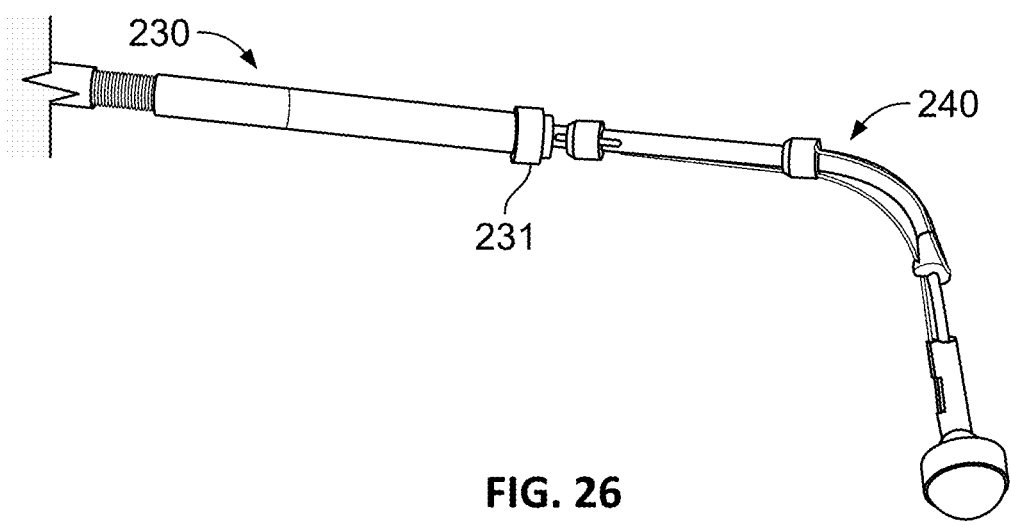

The control handle 210 also includes the second control wire release handle 218 that is used by the clinician user to pull the fifth control wire 247 proximally to release/deploy the posterior arm 150 of the prosthetic heart valve 100. FIGS. 24-26 sequentially illustrate the movements of the distal end portion of the fifth control wire 247 as the clinician user proximally pulls the fifth control wire 247 using the second control wire release handle 218. FIG. 24 shows the distal end portion of the fifth control wire 247 in its initial position in which it is fully engaged with the distal collar 231. In this position, the fifth control wire 247 holds the posterior arm 150 adjacent to the inner control catheter 240 in its low-profile delivery configuration (e.g., as shown in FIG. 15). FIG. 25 shows the fifth control wire 247 just after being disengaged from the distal collar 231.

FIG. 26 shows the fifth control wire 247 further disengaged from the distal collar 231. In this arrangement, the posterior arm 150 is released by the fifth control wire 247 to expand to its fully deployed configuration.

FIGS. 27-36 illustrate a series of steps for deploying a prosthetic heart valve (such as the heart valve 100 described herein in any of its variations) using the heart valve deployment system 200. As a non-limiting example, these figures illustrate a transjugular vein approach to the native tricuspid valve 10 (via the superior vena cava).

Figure 27:
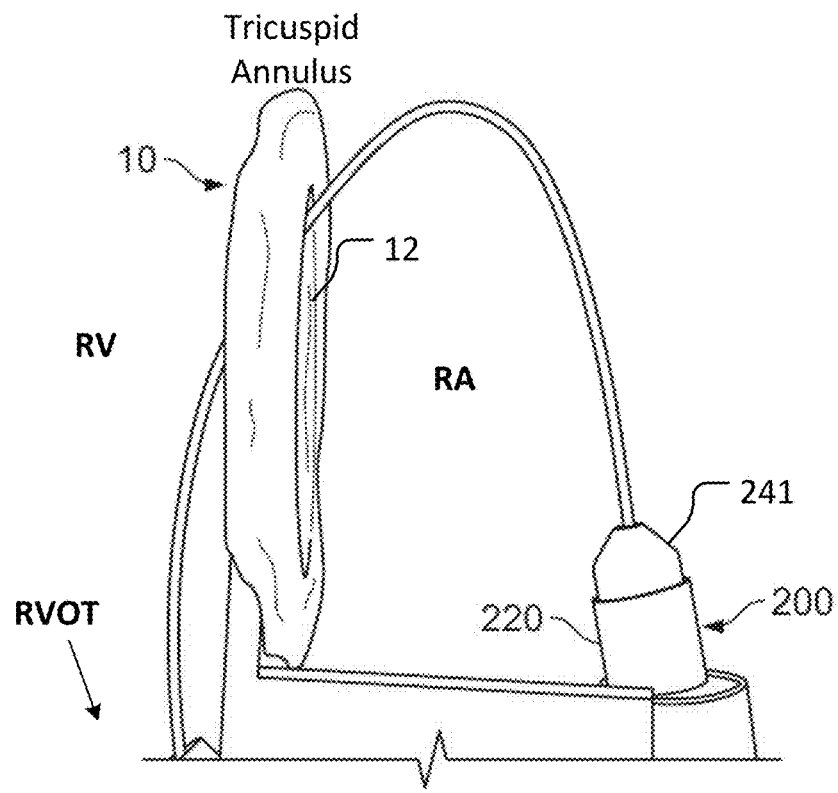
FIGS. 27 through 36 show an example transjugular method of deploying the prosthetic tricuspid valves described herein using the prosthetic heart valve deployment system of FIG. 8.

FIG. 27 shows a distal end portion of the deployment system 200 emerging into the right atrium via the superior vena cava. (Note, this depicts a simplified model that shows the annulus 12 of the native tricuspid valve 10 and not the entire anatomy of the valve 10.) The deployment system 200 is being advanced over a guidewire that was installed previously. The valve 100 (not visible) is within the outer sheath catheter 220 and coupled to the inner control catheter 240 and the middle deflectable catheter 230.

Figure 28:
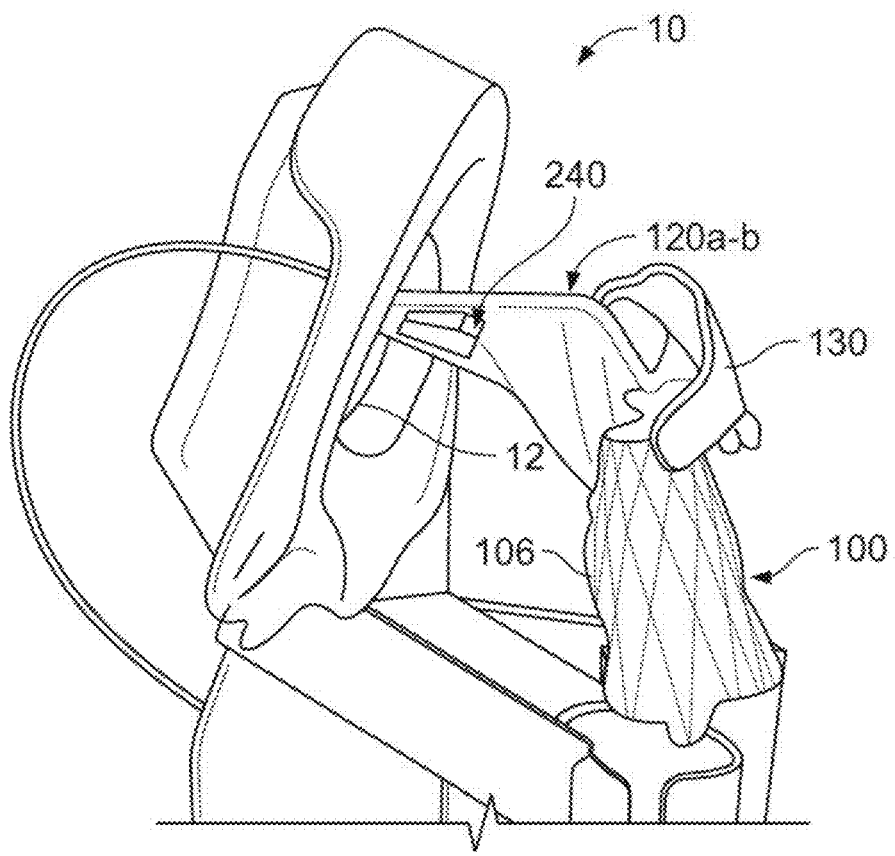

FIG. 28 illustrates the valve 100 (while the valve 100 is releasably coupled to the inner control catheter 240) after the withdrawal of the outer sheath catheter 220 and/or the advancement of the inner control catheter 240 and the middle deflectable catheter 230. At this stage, the curved portion 242 (not visible under the valve 100) has become unconstrained and has elastically deflected to its natural curved configuration. The natural curved configuration of the curved portion 242 facilitates the inner control catheter 240 to make a relatively tight turn within the right atrium to advance from the vena cava and through the annulus 12 of the native tricuspid valve 10 as depicted.

Figure 37:
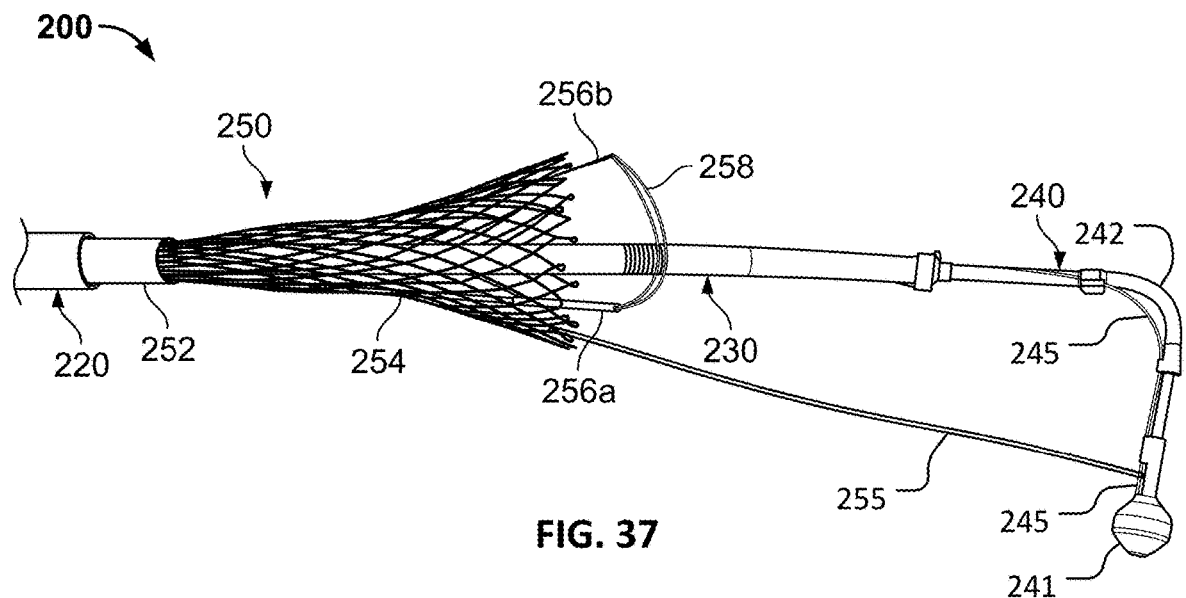
FIG. 37 shows the distal end portion of an example retrieval catheter that is included in some embodiments of the prosthetic heart valve deployment system of FIG. 8.

Referring also to FIG. 37 briefly, in some cases an additional curve (or a controllably adjustable curve) of the curved portion 242 can be needed or desired during the deployment of the valve 100. In such a case, some embodiments include a suture (or wire) member 255 that extends from the retrieval catheter 250 to the third control wire 245 that is engaged with the distal tip member 241. In that arrangement, a clinician can manipulate the retrieval catheter 250 (e.g., pull it proximally) to add tension to the suture member 255 to increase the curvature of the curved portion 242 of the inner control catheter 240. In other words, by manipulating the retrieval catheter 250 to add tension to the suture member 255 a clinician can increase the curvature of the inner control catheter 240 (to be bent beyond the natural curvature of the inner control catheter 240). This can be beneficial as the inner control catheter 240 is manipulated to make the tight turn within the right atrium to advance from the vena cava and through the annulus 12 of the native tricuspid valve 10. After that advancement, and at the appropriate time, the third control wire 245 can be pulled to disengage the suture member 255 from the third control wire 245.

Figure 29:
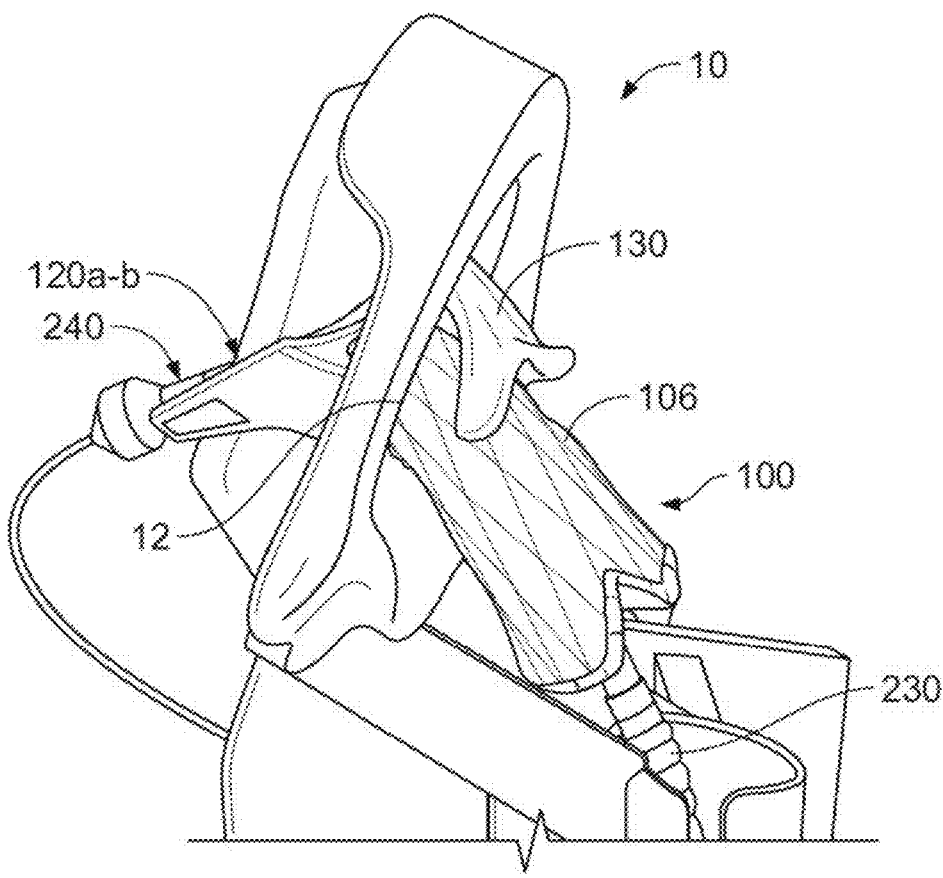
Figure 30:
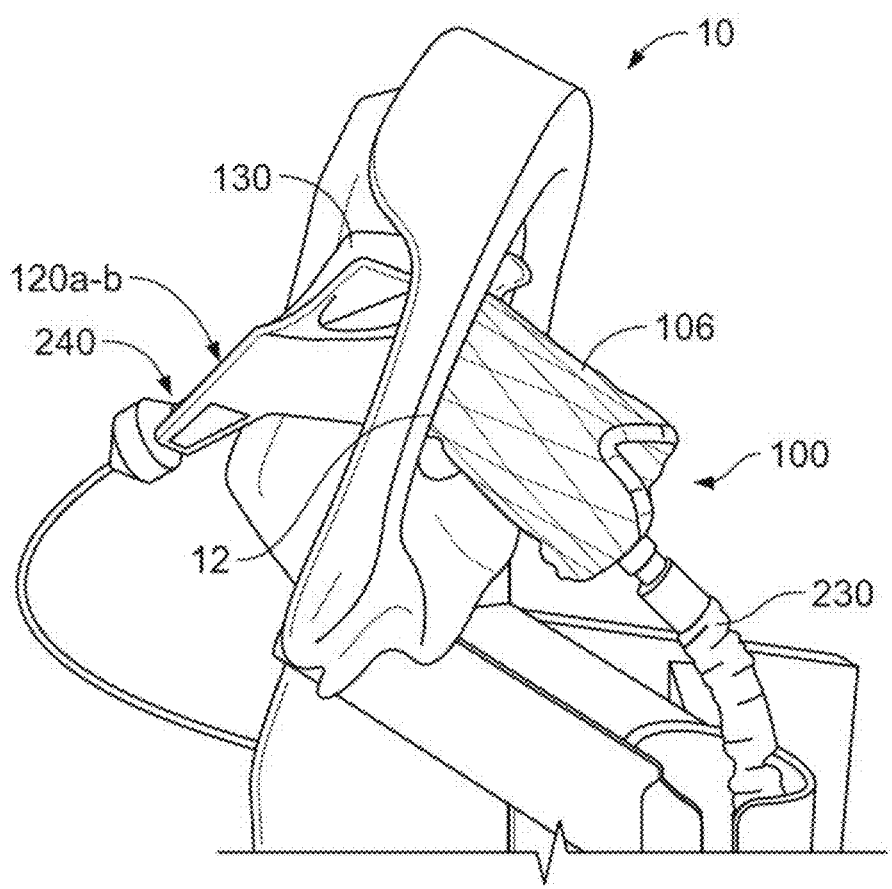

Further describing the series of steps for deploying the prosthetic heart valve 100 using the heart valve deployment system 200, FIGS. 29 and 30 illustrate further advancement of the valve 100 (while the valve 100 is still releasably coupled to the inner control catheter 240). In these images, the middle deflectable catheter 230 is being deflected (by a first amount in FIG. 29 and a greater amount in FIG. 30). The deflection of the middle deflectable catheter 230 adds to the curvature of the inner control catheter 240 to enable the distal end portion of the inner control catheter 240 to become directed toward the RVOT after passing through the annulus 12 (as shown in FIG. 30).

Figure 31:
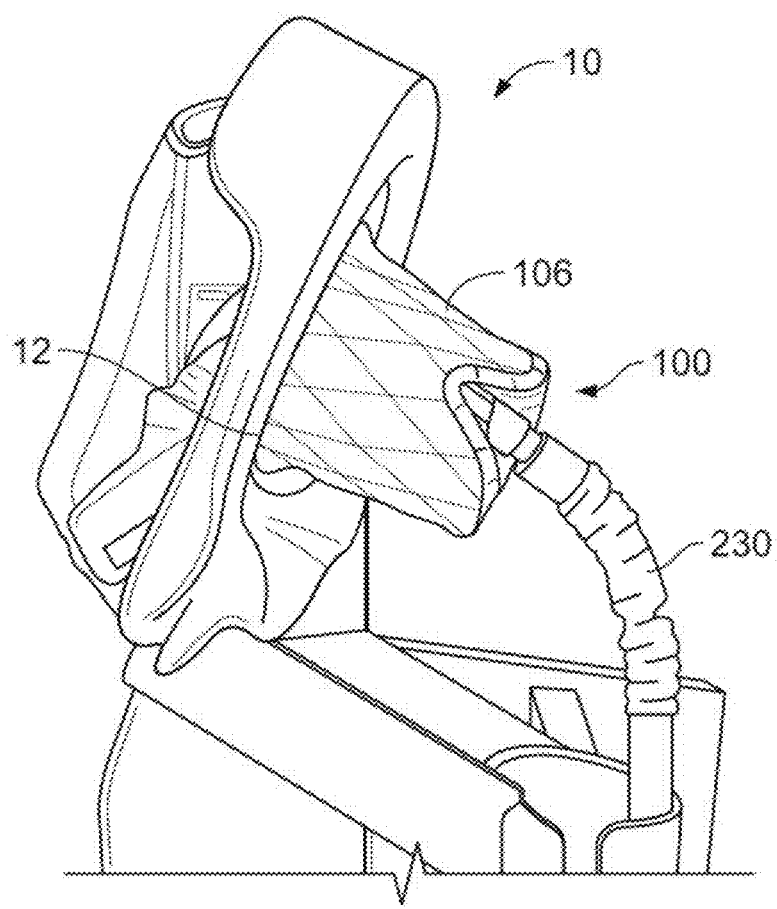
Figure 32:
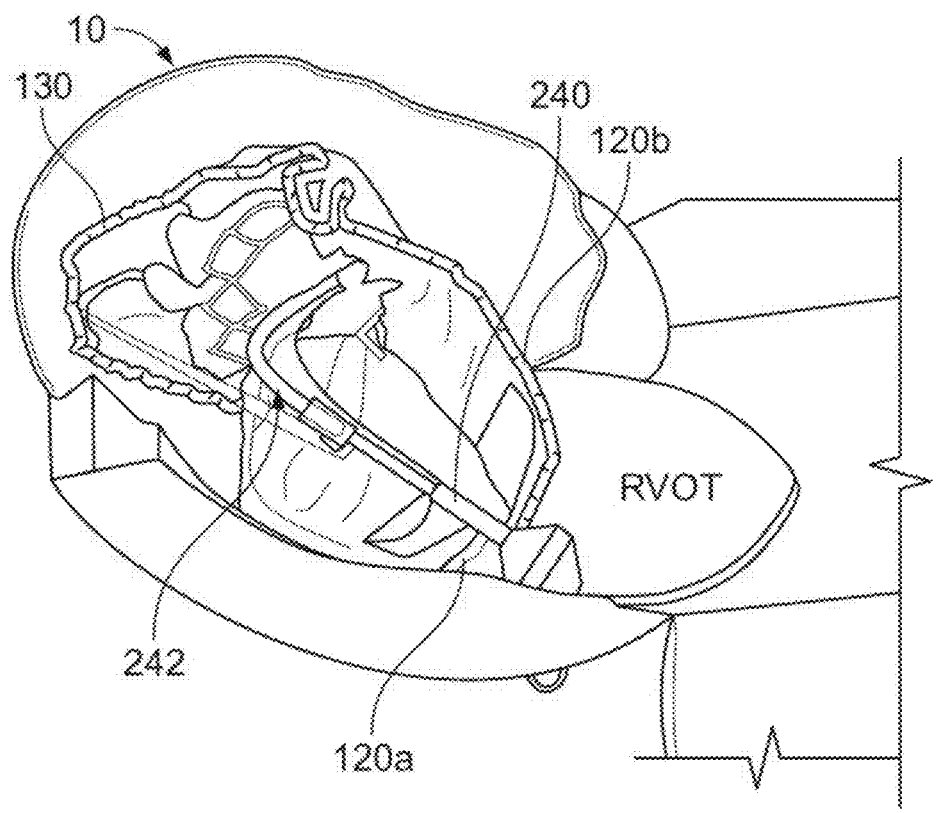
Figure 33:
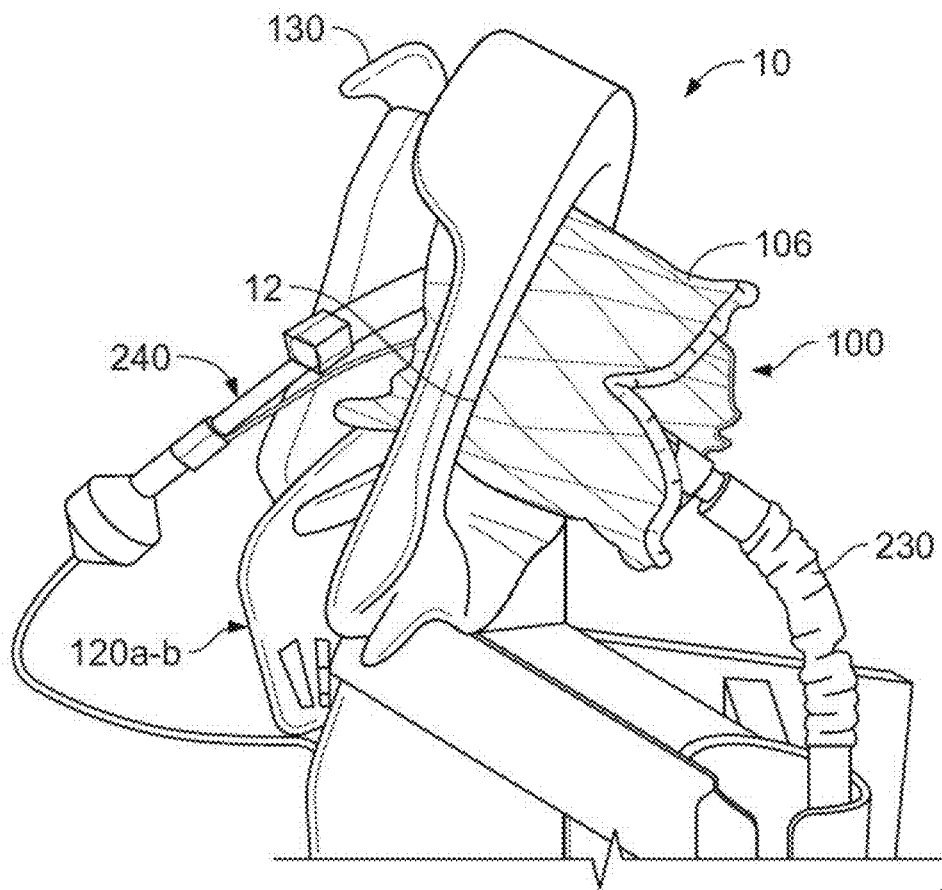

FIGS. 31 through 33 illustrate the release process of the portions of the valve 100 from the inner control catheter 240 and middle deflectable catheter 230. As the portions of the valve 100 are released, those portions become engaged in the targeted native anatomical locations. In some embodiments, the sequence for releasing/deploying the various portions of the valve 100 can be: (i) release of the outflow end portion 1020 of the main body 106, (ii) release of the posterior flap 130, (iii) release of the inflow end portion 102i of the main body 106, (iv) release of the one or more anterior flaps 120a-b, and (v) release of the posterior arm 150. In some embodiments, other release sequences can be used.

At each step of the release/deployment process, the individual portions of the valve 100 can be allowed to expand, and prior to full release of the portion, the clinician user can evaluate the positioning and efficacy of the portion. If the clinician user finds the positioning and efficacy of the portion to be satisfactory, then the clinician user can fully release the portion of the valve 100. However, if the clinician user is not satisfied, then the clinician user can reapply tension to the corresponding control wire and make positioning adjustments prior to again relieving tension of the corresponding control wire to allow the portion of the valve 100 to expand once again.

The control wires and/or release pins for the anterior flaps 120a-b and the posterior flap 130 are released (as best seen in FIG. 32, which is a view from the ventricle towards the native tricuspid valve 10). In response, the anterior flaps 120a-b deploy into the RVOT and the posterior flap 130 deploys to the posterior area of the tricuspid valve 10 just inferior to the annulus 12. In addition, as the posterior flap 130 deploys, the one or more leaflet engagement members 140 become coupled with the posterior leaflet 11p and/or the septal leaflet 11s to provide migration resistance for the valve 100. At this stage, the posterior arm 150 and/or the anterior arm 160 (FIGS. 4-7) can also be deployed if the valve 100 includes a posterior arm 150 and/or an anterior arm 160. FIG. 33 shows the full release of control wires that are coupled to the main body 106. In response, the main body 106 radially expands into contact and engagement with the annulus 12.

Figure 34:
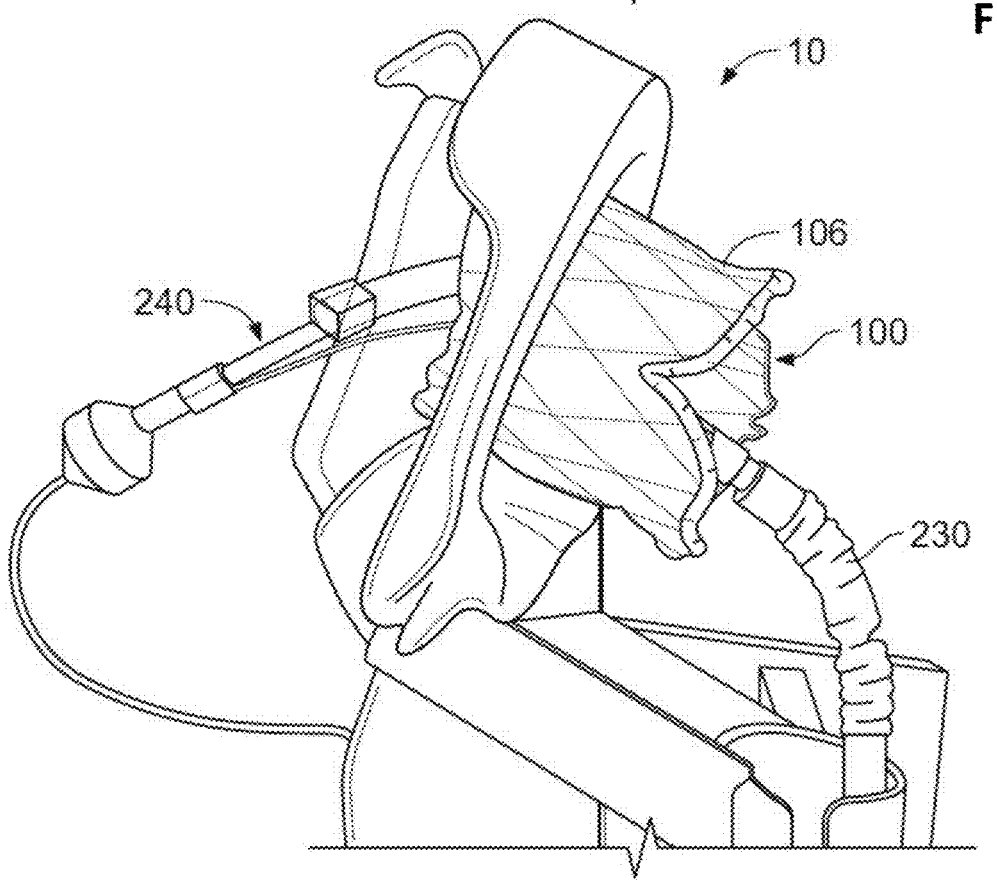
Figure 35:
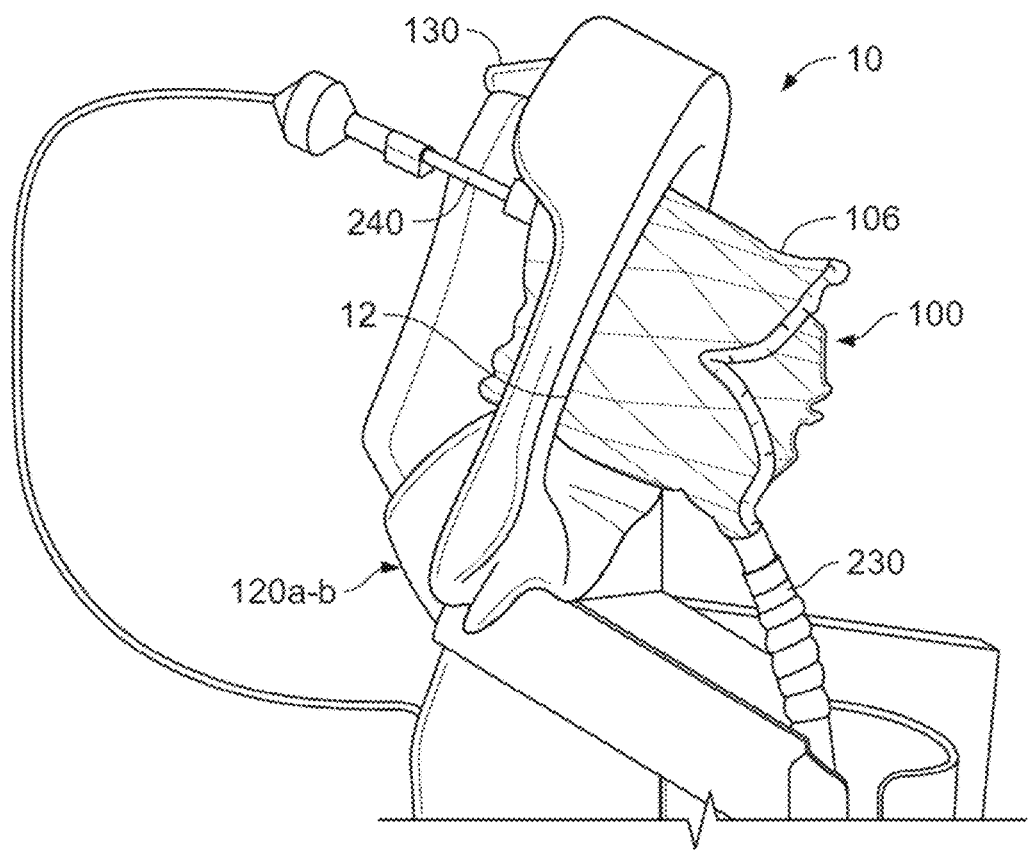
Figure 36:
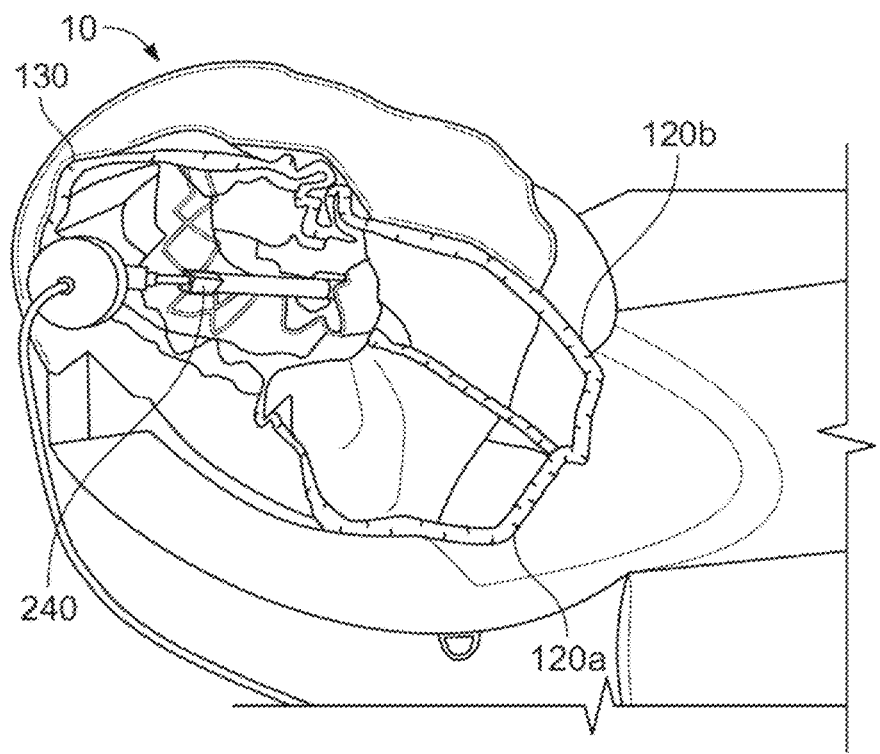

FIGS. 34 through 36 illustrate withdrawal of the deployment system 200. When the control wires are disengaged from the valve 100, the inner control catheter 240 and the middle deflectable catheter 230 can then be withdrawn, leaving the valve 100 engaged with the anatomy in and around the native tricuspid valve 100.

With the deployment system 200 and guidewire fully withdrawn, the implanted heart valve 100 is in engagement with the heart 1 and functioning as a prosthetic tricuspid valve between the RA and the RV. In some embodiments, the heart valve 100 is positioned such that the main body 106 is positionally biased toward the anterior portion of the annulus 12, which is adjacent the RVOT. Accordingly, the laterally-extending posterior flap 130 can help to cover and fluidly seal the native tricuspid valve opening within the annulus 12, which is not circular in some patients (e.g., with the native valve opening being oblong, oval, or irregularly shaped). In other words, in combination with the main body 106 of the valve 100, the posterior flap 130 (and, in some cases, the laterally-extending anterior anchoring flaps 120a-b to a lesser extent) help to cover/occlude and fluidly seal the native tricuspid valve opening which is not circular in some anatomies. In addition, the end portion of the posterior flap 130 extends into engagement with the posterior shelf 11 (FIG. 5) and/or with the wall of the RV just inferior to the annulus 12 to provide anchoring and migration resistance. Accordingly, the posterior flap 130 can perform both sealing and anchorage.

FIGS. 37-44 sequentially illustrate a process of retrieving the prosthetic heart valve 100. This retrieval process can take place after the expression of the valve 100 from the outer sheath catheter 220, but prior to the release of the valve 100 from the control wires. Such a retrieval process may be beneficial, for example, if the clinician user has relaxed one or more of the looped control wires 243, 244, and 246 (FIG. 9) and then finds that the valve 100 would not be suitable for full deployment, for whatever reason. In such a case, the clinician user can reapply the tension to the control wires 243, 244, and 246, and then proceed with the illustrated retrieval process.

As shown in FIG. 37, in some embodiments the deployment system 200 can include a retrieval catheter 250. That is, the deployment system 200 can include the retrieval catheter 250 in addition to the control handle 210 (not shown), the outer sheath catheter 220, the middle deflectable catheter 230, the inner control catheter 240, and the control wires 243, 244, 245, 246, and 247.

In the depicted embodiment, the retrieval catheter 250 includes a catheter shaft 252, a funnel-shaped member 254, two snare arms 256a-b, and a snare wire 258. The funnel-shaped member 254 is attached at a distal end portion of the catheter shaft 252. The snare arms 256a-b and the snare wire 258 are positioned within, and distally extend from, the funnel-shaped member 254.

The catheter shaft 252 of the retrieval catheter 250 defines a lumen. The middle deflectable catheter 230 extends within the lumen of the catheter shaft 252, and extends within the funnel-shaped member 254. The inner control catheter 240 extends within the lumen of the middle deflectable catheter 230. The retrieval catheter 250 extends within the lumen of the outer sheath catheter 220.

In some embodiments, the retrieval catheter 250 is only expressed from the outer sheath catheter 220 if/when the clinician user desires to initiate the valve retrieval process. Otherwise, the clinician user can keep the outer sheath catheter 220 remaining over the funnel-shaped member 254.

In some embodiments, the funnel-shaped member 254 is self-expandable. That is, when the funnel-shaped member 254 is expressed from the confines of the outer sheath catheter 220, the funnel-shaped member 254 will self-expand from its low-profile delivery configuration to its expanded conical shape as shown. In some embodiments, the funnel-shaped member 254 is constructed of a wire framework. For example, in some embodiments the funnel-shaped member 254 has a stent-like construction. In some such embodiments, the funnel-shaped member 254 can be constructed of a metal tube (e.g., Nitinol, stainless steel, alloy steel, titanium, etc.) that is laser cut and shape set into the conical shape as shown.

In some embodiments, the two snare arms 256*a*-*b* are arranged on opposite sides of the deflectable catheter 230 (e.g., at approximately 180° opposite of each other). The snare wire 258 extends between the distal ends of the snare arms 256*a*-*b* to form a loop, and also extends proximally to the control handle 210 (not shown). Accordingly, the clinician user can proximally pull on the snare wire 258 to cinch the looped snare wire 258 between the snare arms 256*a*-*b* to a smaller diameter.

Figure 38:
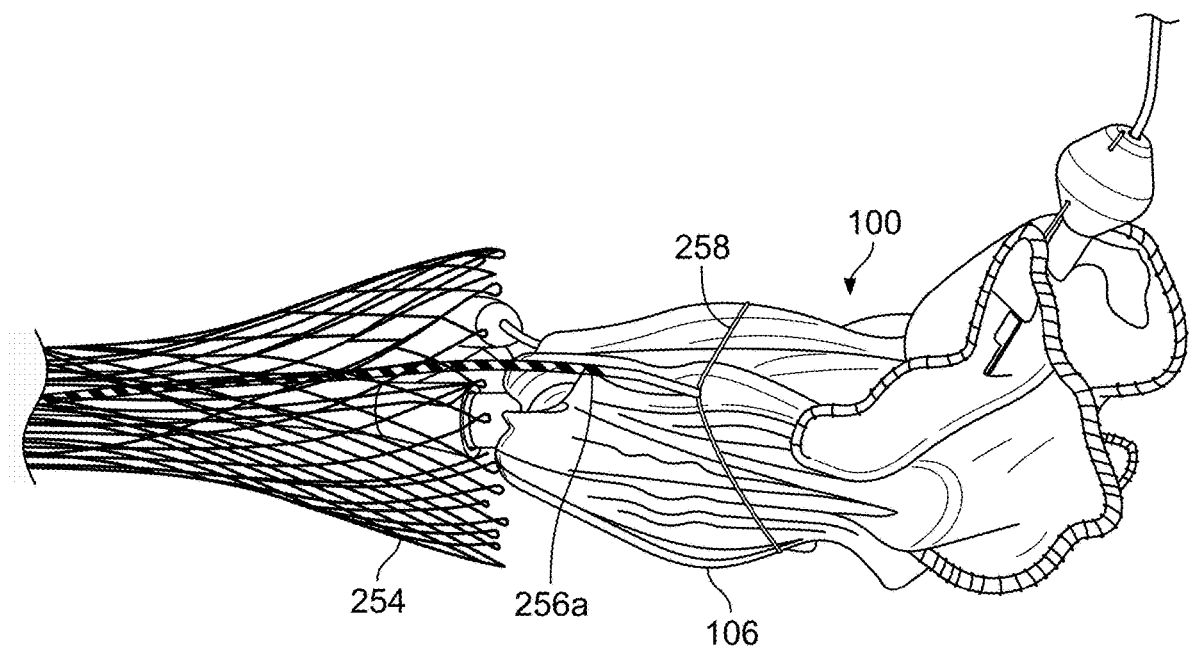
FIGS. 38-44 sequentially illustrate the retrieval catheter of FIG. 37 being used to recapture a prosthetic heart valve in accordance with some implementations.

FIG. 38 shows the snare wire 258 being positioned around the main body 106 of the prosthetic heart valve 100. To achieve this arrangement, the valve 100 is pulled proximally to position it within the looped snare wire 258.

Figure 39:
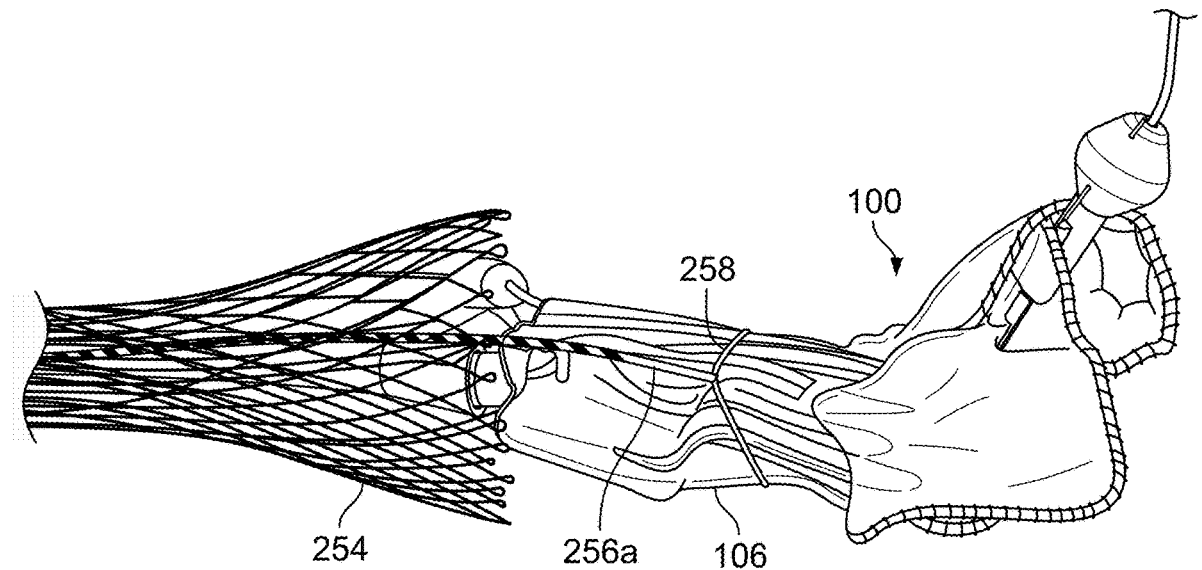
Figure 40:
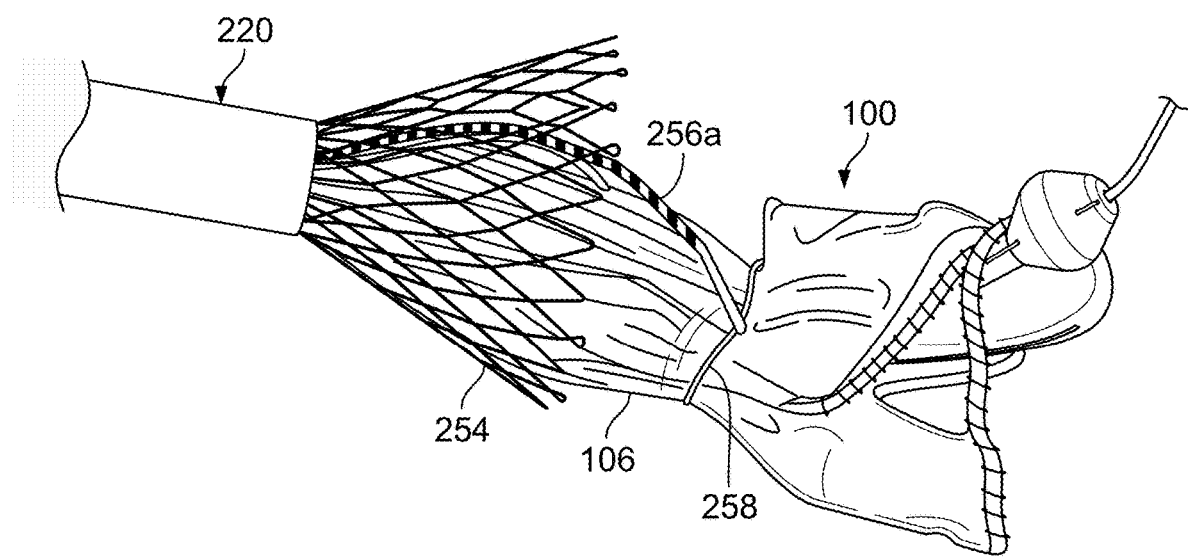

FIG. 39 shows the snare wire 258 being cinched (tightened) around the main body 106 of the prosthetic heart valve 100. The cinching reduces the outer diameter of the valve 100 so that the valve 100 can be pulled within the interior of the expanded funnel-shaped member 254.

Figure 41:
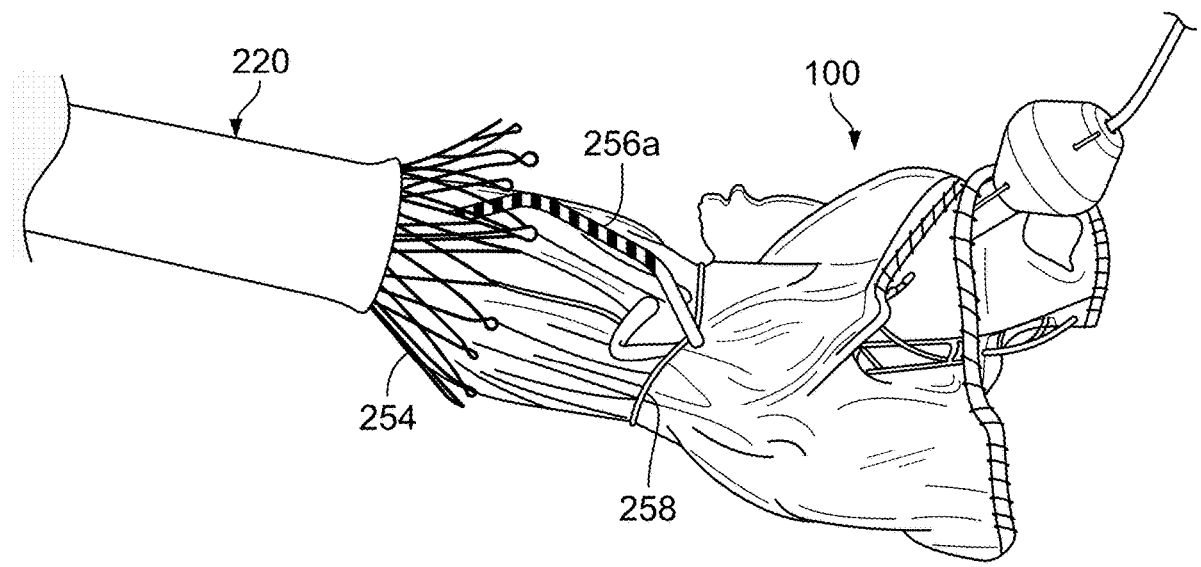
Figure 42:
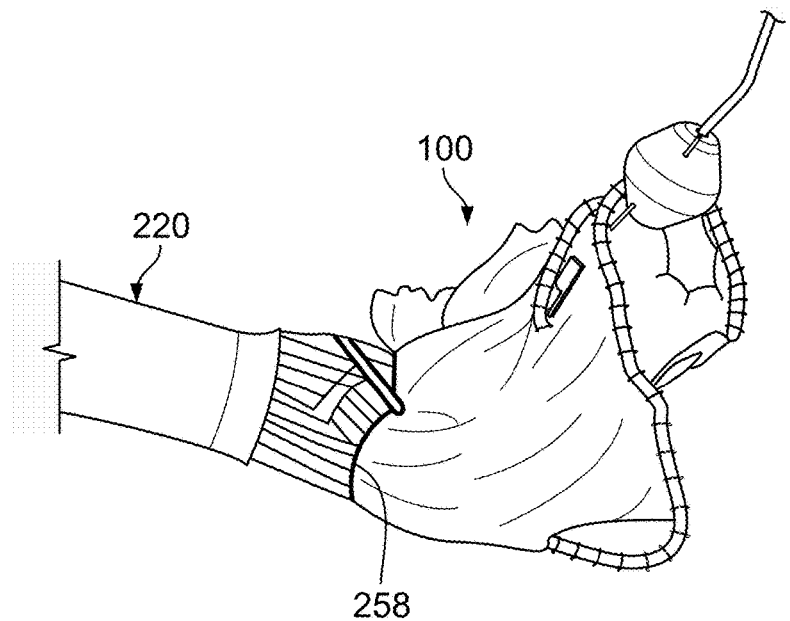
Figure 43:
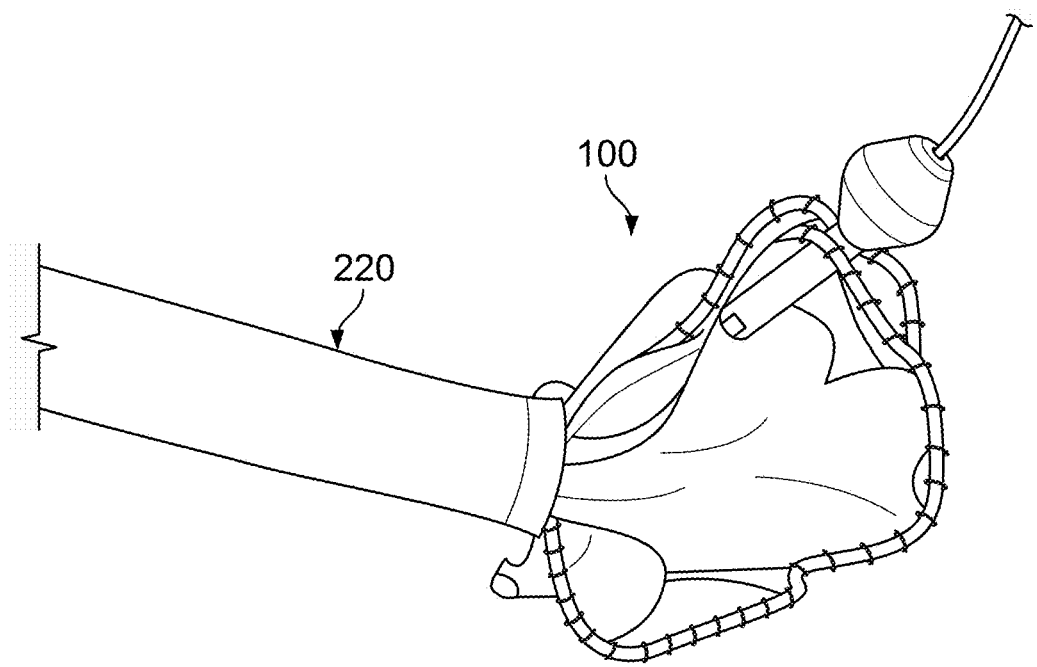
Figure 44:
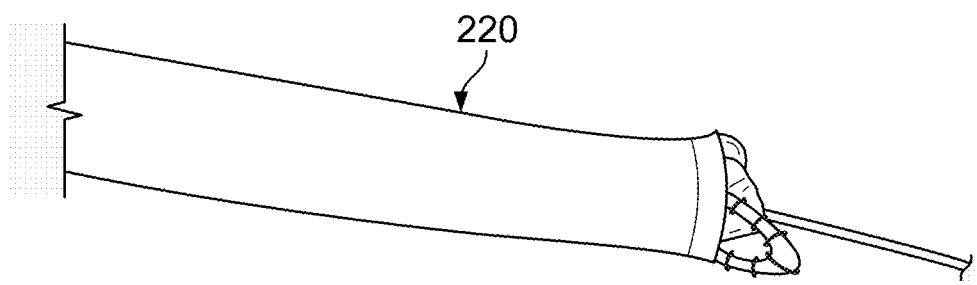

FIG. 41 shows the prosthetic heart valve 100, while cinched to a reduced outer diameter, being pulled into the funnel-shaped member 254.

FIGS. 41-44 progressively show the final steps of the retrieval process as the funnel-shaped member 254 and the prosthetic heart valve 100 are being pulled into the outer sheath catheter 220. This can be performed by the clinician user pulling the inner catheter 240, the middle deflectable catheter 230, and the retrieval catheter 250 proximally in relation to the outer sheath catheter 220.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the steps depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A prosthetic valve system comprising:
   a prosthetic heart valve comprising:
   a main body including an inflow end portion and an outflow end portion, the main body defining a central axis extending between the inflow and outflow end portions; and
   one or more anterior flaps extending from the outflow end portion in a first direction that is transverse to the central axis; and
   a valve deployment system comprising:
   an elongate control catheter defining one or more lumens and comprising a naturally curved end portion;
   a third control wire slidably disposed in the one or more lumens and releasably coupled to the one or more anterior flaps; and
   a suture or wire member releasably coupled to the third control wire,
   wherein adding tension to the suture or wire member adjusts a curvature of the elongate control catheter in a direction of the one or more anterior flaps.

2. The prosthetic valve system of claim 1, further comprising a retrieval catheter with an expandable conical end portion, and wherein the suture or wire member is attached to the retrieval catheter.

3. The prosthetic valve system of claim 1, wherein the inflow end portion of the main body has a smaller outer size than an outer size of the outflow end portion of the main body.

4. The prosthetic valve system of claim 1, wherein the valve deployment system further comprises a first control wire comprising a first wire loop that extends out of the one or more lumens and that is releasably coupled to the inflow end portion of the main body.

5. The prosthetic valve system of claim 1, wherein the valve deployment system further comprises a second control wire comprising a second wire loop that extends out of the one or more lumens and that is releasably coupled to the outflow end portion.

6. The prosthetic valve system of claim 1, wherein the third control wire comprises a single wire segment that extends out of the one or more lumens, releasably couples with the one or more anterior flaps and the suture or wire member, and terminates in releasable engagement with a distal tip portion of the control catheter.

7. The prosthetic valve system of claim 1, wherein the valve deployment system further comprises a deflectable catheter defining a lumen, and wherein a portion of the control catheter is slidably disposable within the lumen of the deflectable catheter.

8. The prosthetic valve system of claim 7, wherein the valve deployment system further comprises a fifth control wire slidably coupled with the deflectable catheter.

9. The prosthetic valve system of claim 8, wherein the prosthetic heart valve further comprises a posterior arm extending from the inflow end portion of the main body.

10. The prosthetic valve system of claim 9, wherein the fifth control wire comprises a single wire segment that releasably couples with the posterior arm and terminates in releasable engagement with a distal tip portion of the deflectable catheter.

11. The prosthetic valve system of claim 7, wherein a distal end portion of the deflectable catheter is selectively deflectable by manipulating a user control mechanism coupled to a proximal end of the valve deployment system.

12. The prosthetic heart valve of claim 1, wherein the one or more anterior flaps comprises a septal anterior flap and a lateral anterior flap, wherein an edge portion of the septal anterior flap comprises a septal anterior strut framework, and wherein an edge portion of the lateral anterior flap comprises a lateral anterior strut framework.

13. The prosthetic heart valve of claim 12, wherein the septal anterior strut framework comprises S-shaped struts, and wherein the lateral anterior strut framework comprises L-shaped struts.

14. The prosthetic heart valve of claim 1, wherein the outflow end portion of the main body extends to a farthest end of the prosthetic heart valve.

* * * * *